US007192708B2

(12) United States Patent
Lu et al.

(10) Patent No.: US 7,192,708 B2
(45) Date of Patent: *Mar. 20, 2007

(54) NUCLEIC ACID ENZYME BIOSENSORS FOR IONS

(75) Inventors: Yi Lu, Champaign, IL (US); Jing Li, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/702,676

(22) Filed: Nov. 6, 2003

(65) Prior Publication Data
US 2004/0161778 A1 Aug. 19, 2004

Related U.S. Application Data

(62) Division of application No. 09/605,558, filed on Jun. 27, 2000, now Pat. No. 6,706,474.

(51) Int. Cl.
C12Q 1/68 (2006.01)
C07H 21/04 (2006.01)
C12P 19/34 (2006.01)

(52) U.S. Cl. .................. 435/6; 536/23.1; 536/24.5; 435/91.2

(58) Field of Classification Search .................. 435/6; 536/23.1, 24.5
See application file for complete search history.

(56) References Cited

U.S. PATENT DOCUMENTS

| 5,459,040 | A | 10/1995 | Hammock et al. |
| 5,472,881 | A | 12/1995 | Beebe et al. |
| 5,580,967 | A | 12/1996 | Joyce |
| 5,593,835 | A | 1/1997 | Rando et al. |
| 5,663,064 | A | 9/1997 | Burke et al. |
| 5,807,718 | A | 9/1998 | Joyce et al. |
| 5,989,813 | A | 11/1999 | Gerdes |
| 6,040,138 | A * | 3/2000 | Lockhart et al. ............ 435/6 |
| 6,110,462 | A | 8/2000 | Barbas et al. |
| 6,361,944 | B1 | 3/2002 | Mirkin et al. |
| 6,451,535 | B1 | 9/2002 | Jenne et al. |
| 6,630,306 | B1 | 10/2003 | Breaker |
| 6,706,474 | B1 | 3/2004 | Lu et al. |
| 2003/0215810 | A1 | 11/2003 | Lu et al. |

FOREIGN PATENT DOCUMENTS

| EP | 121970 | 10/1984 |
| EP | 1219708 | 7/2002 |
| EP | 1 312 674 | 5/2003 |
| GB | 2339280 | 1/2000 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 9827104 A1 * | 6/1998 |
| WO | WO 98/39484 | 9/1998 |
| WO | WO 98/49346 | 11/1998 |
| WO | WO 99/143338 | 3/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/51665 | 7/2001 |
| WO | WO 01/73123 | 10/2001 |
| WO | WO 02/000006 | 1/2002 |
| WO | WO 02/22882 | 3/2002 |
| WO | WO 03/068963 | 8/2003 |
| WO | WO 03/094838 | 11/2003 |
| WO | WO 03/095648 | 11/2003 |
| WO | 2004/081235 | 9/2004 |

OTHER PUBLICATIONS

Lott et al. Proceedings of the National Academy of Science of the USA, 1998, vol. 95, pp. 542-547.*
Pan et al. Biochemistry, 1992, vol. 31, pp. 3887-3895.*
Definition of the word "ion" printed from Merriam-Webster online dictionary (www.m-w.com) on Jun. 30, 2004.*
Breaker et al. Chemistry & Biology 1994, vol. 1, pp. 223-229.*
International Search Report dated Jan. 15, 2003, for corresponding PCT application No. PCT/US01/20557.
Breaker et al., "A DNA Enzyme that Cleaves RNA," Chem. & Biol., 1994, pp. 223-229, vol. 1.
Chartrand et al., Biochem., 1997, pp. 3145-3150, vol. 36.
Faulhammer et al., "Characterization and Divalent Metal-ion Dependence in In Vitro Selected Deoxyribozymes Which Cleave DNA/RNA Chimeric Oligonucleotides," J. Mol. Biol., 1997, pp. 188-202, vol. 269.
Deo et al., "A Selective, Ratiometric Flourescent Sensor for $Pb^{2+}$," J. Am. Chem. Soc., 2000 pp. 174-175, vol. 122.
Geyer et al., "Lanthanide Probes for a Phosphodiester-Cleaving, Lead-Dependent, DNAzyme," J. Mol. Biol., 1998, pp. 483-489, vol. 275.
Geyer et al., "Evidence for the Metal-Cofactor Independence of an RNA Phosphodiester-Cleaving DNA Enzyme," Chem. & Biol., 1997, pp. 579-593, vol. 4.
Hoogstraten et al., J. Mol. Biol., 1998, pp. 337-350, vol. 284.
Hoogstraten et al., J. Am. Chem. Soc., 2002, pp. 834-842, vol. 124.
Katahira et al., European J. Biochem., 1998, pp. 727-733, Vo. 255.
Khan et al., Nucl. Acid. Res., 1996, pp. 3568-3575, vol. 24.
Kim et al., J. Biochem., 1997, pp. 1062-1067, vol. 122.
Kozumi et al., Allosteric Selection of Ribozymes that Respond to the Second Messengers cGMP and cAMP, Nature Struct. Biol., 1999, pp. 1062-1071, vol. 6.
Legault et al., J. Mol. Biol., 1998, pp. 325-335, vol. 284.

(Continued)

Primary Examiner—James Schultz
Assistant Examiner—Tracy Vivlemore
(74) Attorney, Agent, or Firm—Evan Law Group LLC

(57) ABSTRACT

A method of detecting the presence of an ion includes contacting a nucleic acid enzyme with a sample suspected of containing the ion, where the enzyme contains a ribonucleotide and is dependent on the ion to produce a product from a substrate, and measuring an amount of the product produced. The ion is $Pb^{2+}$, and is in the presence of other ions.

69 Claims, 11 Drawing Sheets

OTHER PUBLICATIONS

Lemieux et al., RNA, 1998, pp. 739-749, vol. 4.
Li et al, "In vitro Selection and Characterization of a Highly Efficient Zn(II)-Dependent RNA-Cleaving Deoxyribozyme," Nucl. Acid. Res., 2000, pp. 481-488, vol. 28.
Liu et al., "A Fiber-Optic Evanescent Wave DNA Biosensor Based on Novel Molecular Beacons," Anal. Chem., pp. 5054-5059, vol. 71.
Mecklenburg et al., Anal. Chimica Acta, 1997, pp. 79-86, vol. 347.
Mullah et al., Tetrahedron Lett., 1997, pp. 5751-5754, vol. 38.
Nazarenko et al., Nucl. Acid. Res., 1997, pp. 2516-2521, vol. 25.
Omichi et al., "Effect of Substrate RNA Sequence on the Cleavage Reaction by a Short Ribozyme," Nucl. Acid Res., 1998, pp. 5655-5661, vol. 26.
Omichi et al., Biochem., 1997, pp. 3514-3521, vol. 36.
Ota et al., "Effects of Helical Structures Formed by the Binding Arms of DNAzymes and Their Substrates on Catalytic Activity," Nucl. Acid. Res., 1998, pp. 3385-3391, vol. 26.
Potyrailo et al., "Adapting Selected Nucleic Acid Ligands (Aptamers) to Biosensors," Anal. Chem., 1998, pp. 3419-3425, vol. 70.
Sabanayagam et al., "Oligonucleotide Immobilization on Micropatterned Streptavidin Surfaces," Nucl. Acid. Res., 2000, vol. 28, 4 pages.
Santoro et al., "Mechanism and Utility of an RNA-Cleaving DNA Enzyme," Biochem., 1998, pp. 13330-13342, vol. 37.
Santoro et al., "A General Purpose RNA-Cleaving DNA Enzyme," Proc. Natl. Acad. Sci. USA, 1997, pp. 4262-4266, vol. 94.
Scott, Current Opinion in Structural Biology, 1998, pp. 337-350, vol. 8.
Stojanovic et al., "Aptamer-Based Folding Fluorescent Sensor for Cocaine," J. Am. Chem. Soc., 2001, pp. 4928-4931, vol. 122.
Stojanovic et al., "Fluorescence Sensors Based on Aptamer Self-Assembly," J. Am. Chem. Soc., 2000, pp. 11547-11548, vol. 123.
Streicher et al., Nucl. Acid. Res., 1993, pp. 311-317, vol. 21.
Sugimoto et al., FEBS Lett., 1996, pp. 96-100, vol. 393.
Walter et al., "Folding of the Four-Way Junction of the Hairpin Ribozyme," Biochem., 1998, pp. 17629-17636, vol. 37.
Wedekind et al., Nature Structural Biology, 1999, pp. 261-268, vol. 6.
Williams et al., EMBO J., pp. 4551-4557, vol. 14.
Abstract of Joyce, G., "Design and catalytic activity of enzyumic DNA molecules"., (1998).
Allara, D. et al., "Spontaneously organized molecular assemblies. 1.Formation, dynamics and physical properties of n-alkanoic acids adsorbed from solution on an oxidized aluminum surface"., Langmuir, vol. 1, No. 1, pp. 45-52, (1985).
Andreola, M-L., et al., "DNA aptamers selected against the HIV-1 RNase H display in vitro antiviral activity"., Biochemistry, vol. 40, No. 34, pp. 10087-10094, (2001).
Bain, C. D., et al., "Modeling organic surfaces with self-assembled monolayers"., Angew. Chem. Int. Ed. Engl., vol. 28, No. 4, pp. 506-512, (1989).
Been, M.D., et al., "Self-cleaving ribozymes of hepatitis delta virus RNA"., Eur. J. Biochem., vol. 247, pp. 741-753, (1997).
Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).
Blake, D.A., et al., "Antibody-based sensors for heavy metal ions"., Biosensors & Bioelectronics, vol. 16, pp. 799-809, (2001).
Blank, M., et al., "Systematic evolution of a DNA aptamer binding to rat brain tumor microvessels. Selective targeting of endothelial regulatory protein pigpen"., Journal of Biological Chemistry, vol. 276, No. 19, pp. 16464-16468, (2001).
Bock, L.C., et al., "Selection of single-stranded DNA molecules that bind and inhibit human thrombin"., Nature, vol. 355, pp. 564-566, (1992).
Bogden, J.D., et al., "Soil contamination from lead in paint chips"., Bulletin of Environmental Contamination & Toxicology, vol. 14, No. 3, pp. 289-294, (1975).

Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).
Breaker, R.R., "Catalytic DNA: in training and seeking employment"., Nature Biotechnology, vol. 17, pp. 422-423, (1999).
Breaker, R.R., "DNA enzymes"., Nature Biotechnology, vol. 15, pp. 427-431, (1997).
Breaker, R.R., "Molecular Biology: Making Catalytic DNAs"., Science, vol. 290, issue 5499, pp. 2095-2096, (2000).
Breaker, R.R., et al., "A DNA enzyme that cleaves RNA"., Chemistry & Biology, vol. 1, No. 4, pp. 223-229, (1994).
Breaker, R.R., et al., "A DNA enzyme with $Mg^{2+}$-dependent RNA phosphoesterase activity"., Chemistry & Biology, vol. 2, No. 10, pp. 655-660, (1995).
Breaker, R.R., et al., "Engineered allosteric ribozymes as biosensor components"., Current Opinion in Biotechnology, vol. 13, pp. 31-39, (2002).
Brody, E.N., et al., "Aptamers as therapeutic and diagnostic agents"., Reviews in Molecular Biotechnology, vol. 74, pp. 5-13, (2000).
Broude, N.E., "Stem-loop oligonucleotides: a robust tool for molecular biology and biotechnology", Trends in Biotechnology, vol. 20, No. 6, pp. 249-256, (2002).
Brown, A.K., et al., "A lead-dependent DNAzyme with a two-step mechanism"., Biochemsitry, vol. 42, No. 23, pp. 7152-7161, (2003).
Bruesehoff, P. J., et al., "Improving metal ion specificity during In Vitro selection of catalytic DNA"., Combinatorial Chemistry & High Throughput Screening, vol. 5, pp. 327-335, (2002).
Bruno, J.G., et al., "In vitro selection of DNA aptamers to anthrax spores with electrochemiluminescence detection"., Biosensors & Bioelectronics, vol. 14, pp. 457-464, (1999).
Bruno, J.G., et al., "Use of magnetic beads in selection and detection of biotoxin aptamers by electrochemiluminescence and enzymatic methods"., BioTechniques, vol. 32, No. 1, pp. 178-180, pp. 182-183, (2002).
Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).
Burgstaller, P., et al., "Isolation of RNA aptamers for biological cofactors by in vitro selection", Angew. Chem. Int. Ed. Engl, vol. 33, No. 10, pp. 1084-1087, (1994).
Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).
Burke, D.H., et al., "A Novel Acidophilic RNA Motif That Recognizes Coenzyme A"., Biochemistry, vol. 37, No. 13, pp. 4653-4663, (1998).
Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).
Burke, D.H., et al., "RNA aptamers to the peptidyl transferase inhibitor chloramphenicol"., Chemistry & Biology, vol. 4, No. 11, pp. 833-843, (1997).
Burmeister, J., et al., "Cofactor-assisted self-cleavage in DNA libraries with a 3'-5'-phosphoramidate bond"., Angew. Chem. Int. Ed. Engl., vol. 36, No. 12, pp. 1321-1324, (1997).
Burwell Jr., R.L., "Modified silica gels as adsorbents and catalysts"., Chemical Technology, 4, pp. 370-377, (1974).
Cadwell, R.C., et al., "Mutagenic PCR"., PCR Methods and Applications, vol. 3, pp. S136-S140, (1994).
Cadwell, R.C., et al., "Randomization of genes by PCR mutagenesis"., PCR Methods and Applications, vol. 2, pp. 28-33, (1992).
Cao, Y.W., et al., "DNA-modified core-shell Ag/Au nanoparticles"., J. Am. Chem. Soc., vol. 123, No. 32, pp. 7961-7962, (2001).
Carmi, N., et al., "Cleaving DNA with DNA"., Proc. Natl. Acad. Sci. USA, vol. 95, pp. 2233-2237, (1998).
Carmi, N., et al., "In vitro selection of self-cleaving DNAs"., Chemistry & Biology, vol. 3, No. 12, pp. 1039-1046, (1996).

Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).

Cech, T.R., et al., "Group I ribozymes: substrate recognition, catalytic strategies, and comparative mechanistic analysis"., Nucleic Acids and Molecular Biology, vol. 10, pp. 1-17, (1996).

Chaloin, L., et al., "Endogenous expression of a high-affinity pseudoknot RNA aptamer suppresses replication of HIV-1"., Nucleic Acids Research, vol. 30, No. 18, pp. 4001-4008, (2002).

Chapman, K.B., et al., "In vitro selection of catalytic RNAs", Current Opinion in Structural Biology, vol. 4, pp. 618-622, (1994).

Chen, J-H., et al., "A specific quadrilateral synthesized from DNA branched junctions"., J. Am. Chem. Soc., vol. 111, No. 16, pp. 6402-6407, (1989).

Chen, L., et al., "Crystal structure of a four-stranded intercalated DNA: d($C_4$)"., Biochemistry, vol. 33, No. 46, pp. 13540-13546, (1994).

Ciesiolka, J., et al., "Selection of an RNA domain that binds $Zn^{2+}$"., RNA, vol. 1, pp. 538-550, (1995).

Ciesiolka, J., et al., "Small RNA-divalent domains"., RNA, vol. 2, pp. 785-793, (1996).

Conaty, J., et al., "Selected classes of minimised hammerhead ribozyme have very high cleavage rates at low $Mg^{2+}$concentration"., Nucleic Acids Research, vol. 27, No. 11, pp. 2400-2407, (1999).

Conn, M.M., et al., "Porphyrin Metalation Catalyzed by a Small RNA Molecule"., J. Am. Chem. Soc, vol. 118, No. 29, pp. 7012-7013, (1996).

Connell, G.J., et al., "RNAs with dual specificity and dual RNAs with similar specificity"., Science, New Series, vol. 264, issue 5162, pp. 1137-1141, (1994).

Connell, G.J., et al., "Three small ribooligonucleotides with specific arginine sites"., Biochemistry, vol. 32, No. 21, pp. 5497-5502, (1993).

Cuenoud, B., et al., "A DNA metalloenzyme with DNA ligase activity"., Nature, vol. 375, pp. 611-614, (1995).

Czarnik, A.W., "Desperately seeking sensors"., Chemistry & Biology, vol. 2, No. 7, pp. 423-428, (1995).

Dai, X., et al., "Cleavage of an amide bond by a ribozyme"., Science, New Series, vol. 267, issue 5195, pp. 237-240, (1995).

Davis, J.H., et al., "Isolation of high-affinity GTP aptamers from partially structured RNA libraries"., Proc. Natl. Acad. Sci. USA, vol. 99, No. 18, pp. 11616-11621, (2002).

Davis, K.A., et al., "Staining of cell surface human CD4 with 2'-F-pyrimidine-containing RNA aptamers for flow cytometry"., Nucleic Acids Research, vol. 26, No. 17, pp. 3915-3924, (1998).

Definition of the word "ion" printed from Merriam-Webster online dicitionary (www.m-w.com) on Jun. 30, 2004.

Definition of the word"particle" printed from Merriam-Webster online dictionary (www.m-w.com) on Jun. 29, 2004.

Deo, S., et al., "A Selective, Ratiometric Fluorescent Sensor for $Pb^{2+}$" J. Am. Chem. Soc., vol. 122, No. 1, pp. 174-175, (2000).

Derose, V.J., "Two Decades of RNA Catalysis"., Chemistry & Biology, vol. 9, pp. 961-969, (2002).

Didenko, V.V., "DNA probes using fluorescence resonance energy transfer (FRET): Designs and applications"., BioTechniques, vol. 31, pp. 1106-1118, (2001).

Doudna, J.A., et al., "The Chemical Repertoire of Natural Ribozymes"., Nature, vol. 418, pp. 222-228, (2002).

Earnshaw, D.J., et al., "Modified oligoribonucleotides as site-specific probes of RNA structure and function"., Biopolymers (Nucleic Acid Sciences), vol 48, pp. 39-55, (1998).

Ekland, E.H., et al., "RNA-catalysed RNA polymerization using nucleoside triphosphates"., Nature, vol. 382, pp. 373-376, (1996).

Ekland, E.H., et al., "Structurally complex and highly active RNA ligases derived from random RNA sequences"., Science, vol. 269, issue 5222, pp. 364-370, (1995).

Elghanian, R., et al., "Selective colorimetric detection of polynucleotides based on the distance-dependent optical properties of gold nanoparticles"., Science, vol. 277, pp. 1078-1081, (1997).

Ellington, A.D., et al., "Aptamers as potential nucleic acid pharmaceuticals"., Biotechnology Annual Review, vol. 1, pp. 185-214, (1995).

Ellington, A.D., et al., "In vitro selection of RNA molecules that bind specific ligands"., Nature, vol. 346, pp. 818-822, (1990).

Ellington, A.D., et al., "Selection in vitro of single-stranded DNA molecules that fold into specific ligand-binding structures"., Nature, vol. 355, pp. 850-852, (1992).

Famulok, M., "Molecular Recognition of Amino Acids by RNA-Aptamers: An L-Citrulline Binding RNA Motif and Its Evolution into an L-Arginine Binder"., J. Am. Chem. Soc., vol. 116, No. 5, pp. 1698-1706, (1994).

Famulok, M., "Oligonucleotide aptamers that recognize small molecules", Current Opinion in Structural Biology, vol. 9, pp. 324-329, (1999).

Famulok, M., et al., "In Vitro Selection Analysis of Neomycin Binding RNAs with a Mutagenized Pool of Variants of the 16S rRNA Decoding Region"., Biochemistry, vol. 35, No. 14, pp. 4265-4270, (1996).

Famulok, M., et al., "Stereospecific recognition of tryptophan agarose by in vitro selected RNA"., J. Am. Chem. Soc., vol. 114, No. 10, pp. 3990-3991, (1992).

Faulhammer, D., et al., "Characterization and Divalent Metal-ion Dependence of in Vitro Selected Deoxyribozymes which Cleave DNA/RNA Chimeric Oligonucleotides"., J. Mo. Biol., vol. 269, pp. 188-202, (1997).

Faulhammer, D., et al., "The $Ca^{2+}$ion as a cofactor for a novel RNA-cleaving deoxyribozyme"., Angew. Chem., Int. Ed. Engl., vol. 35, No. 23/24, pp. 2837-2841, (1996).

Fodor, S.P.A., et al., "Light-directed, spatially addressable parallel chemical synthesis"., Science, New Series, vol. 251, issue 4995, pp. 767-773. (1991).

Frank, D.N., et al., "In vitro selection for altered divalent metal specificity in the RNase P RNA"., Proc. Natl. Acad. Sci. USA, vol. 94, pp. 14355-14360, (1997).

Frens, G., et al., "Controlled Nucleation for the regulation of the particle size in monodisperse gold suspensions"., Nature Physical Sicence, vol. 241, pp. 20-22, (1973).

Fukusaki, E-I., et al., "DNA aptamers that bind to chitin"., Bioorganic & Medicinal Chemsitry letters, vol. 10, pp. 423-425, (2000).

Geiger, A., et al., "RNA aptamers that bind L-arginine with sub-micromolar dissociation constants and high enantioselectivity"., Nucleic Acids Research, vol. 24, No. 6, pp. 1029-1036, (1996).

Geyer, C.R., et al., "Evidence for the metal-cofactor independence of an RNA phosphodiester-cleaving DNA enzyme"., Chemistry & Biology, vol. 4, No. 8, pp. 579-593, (1997).

Geyer, C.R., et al., "Lanthanide Probes for a Phosphodiester-cleaving, Lead-dependent, DNAzyme"., J. Mol. Biol., vol. 275, pp. 483-489, (1998).

Giver, L., et al., "Selection and design of high-affinity RNA ligands for HIV-1 Rev"., Gene, vol. 137, pp. 19-24, (1993).

Giver, L., et al., "Selective optimization of the Rev-binding element of HIV-1"., Nucleic Acids Research, vol. 21, No. 23, pp. 5509-5516, (1993).

Godwin, H.A., et al., "A Flourescent Zinc Probe Based on Metal-Induced Peptide Folding"., J. Am. Chem. Soc., vol. 118, pp. 6514-6515, (1996).

Grabar, K., et al., "Preparation and characterization of Au colloid Monolayers"., Analytical chemistry, vol. 67, No. 4, pp. 735-743, (1995).

Grate, D., et al., "Laser-mediated, site-specific inactivation of RNA transcripts"., Proc. Natl. Acad. Sci. USA, vol. 96, pp. 6131-6136, (1999).

Guschin, D., et al., "Manual manufacturing of oligonucleotide, DNA, and protein microchips"., Analytical Biochemistry, vol. 250, pp. 203-211, (1997).

Haller, A.A., et al., "In vitro selection of a 7-methyl-guanosine binding RNA that inhibits translation of capped mRNA molecules"., Proc. Natl. Acad. Sci. USA, vol. 94, pp. 8521-8526, (1997).

Harada, K., et al., "Identification of two novel arginine binding DNAs"., The EMBO Journal, vol. 14, No. 23, pp. 5798-5811, (1995).

Hennrich, G., et al., "Redox switchable fluorescent probe selective for either Hg(II) or Cd(II) and Zn(II)" J. Am. Chem. Soc., vol. 121, No. 21, pp. 5073-5074. (1999).

Hesselberth, J., et al., "In vitro selection of nucleic acids for diagnostic applications"., Reviews in Molecular Biotechnology, vol. 74, pp. 15-25, (2000).

Hesselberth, J.R., et al., "Simultaneous detection of diverse analytes with an aptazyme ligase array", Analytical Biochemistry vol. 312, pp. 106-112, (2003).

Ho, H-A., et al., "Optical sensors based on hybrid aptamer/conjugated polymer complexes"., J. Am. Chem. Soc., vol. 126, No. 5, pp. 1384-1387, (2004).

Hofmann, H.P., et al., "$Ni^{2+}$-binding RNA motifs with an asymmetric purine-rich internal loop and a G-A base pair"., RNA, vol. 3, pp. 1289-1300, (1997).

Holeman, L.A., et al., "Isolation and characterization of fluorophore-binding RNA aptamers"., Folding & Design, vol. 3, pp. 423-431, (1998).

Hoogstraten, C.G., et al., "Structural analysis of metal ion ligation to nucleotides and nucleic acids using pulsed EPR spectroscopy"., J. Am. Chem. Soc., vol. 124, No. 5, pp. 834-842, (2002).

Huizenga, D.E., et al., "A DNA aptamer that binds adenosine and ATP"., Biochemistry, vol. 34, No. 2, pp. 656-665, (1995).

Iler, R.K., "The Chemistry of Silica: Solubility, Polymerization, Colloid and Surface Properties, and Biochemistry, Chapter 6, The surface chemsitry of silica"., pp. 622-729, A Wiley-Interscience Publication, New York, (1979).

Illangasekare, M., et al., "Small-molecule-substrate interactions with a self-aminoacylating ribozyme"., J. Mol. Biol., vol. 268, pp. 631-639, (1997).

Imperiali, B., et al., "Peptide platforms for metal ion sensing"., Proc. SPIE-The international society for optical engineering, vol. 3858, pp. 135-143, (1999).

International Search Report dated Jan. 15, 2003 for corresponding PCT application No. PCT/US01/20557.

International Search Report dated Aug. 1, 2003 for corresponding PCT application No. PCT/US03/08483.

Jayasena, S.D., "Aptamers: an emerging class of molecules that rival antibodies in diagnostics"., Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA"., Science, vol. 263, pp. 1425-1429, (1994).

Jenne, A., et al., "Rapid Identification and Characterization of Hammerhead-Ribozyme Inhibitors Using Fluorescence-Based Technology"., Nature Biotechnology, vol. 19, pp. 56-61, (2001).

Jenne, A., et al., "Real-time characterization of Ribozymes by Fluorescence Resonance Energy Transfer (FRET)"., Angewandte Chemie. International Edition, vol. 38, No. 9, pp. 1300-1303, (1999).

Jhaveri, S., et al., "In vitro selection of signaling aptamers"., Nature Biotechnology, vol. 18, pp. 1293-1297, (2000).

Jhaveri, S.D., et al., "Designed signaling aptamers that transduce molecular recognition to changes in fluorescence intensity"., J. Am. Chem. Soc., vol. 122, No. 11, pp. 2469-2473, (2000).

Joos, B., et al., "Covalent attachment of hybridizable oligonucleotides to glass supports"., Analytical Biochemsitry, vol. 247, pp. 96-101, (1997).

Josephson, L., et al., "Magnetic nanosensors for the detection of oligonucleotide sequences"., Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids"., Current Opinion in Structural Biology, vol. 4, pp. 331-336, (1994).

Kato, T., et al., "In vitro selection of DNA aptamers which bind to cholic acid"., Biochimica et Biophysica Acta, vol. 1493, pp. 12-18, (2000).

Kawakami, J., et al., "In vitro selection of aptamers that act with $Zn^{2+}$"., Journal of Inorganic Biochemistry, vol. 82, pp. 197-206, (2000).

Kiga, D., et al., "An RNA aptamer to the xanthine/guanine base with a distinctive mode of purine recognition"., Nucleic Acids Research, vol. 26, No. 7, pp. 1755-1760, (1998).

Klussmann, S., et al., "Mirror-image RNA that binds D-adenosine"., Nature Biotechnology, vol. 14, pp. 1112-1115, (1996).

Kohama, T., et al., "Molecular Cloning and Functional Characterization of Murine Sphingosine Kinase", The Journal of Biological Chemsitry, vol. 273, No. 37, pp. 23722-23728, (1998).

Koizumi, M., et al., "Allosteric Selection of Ribozymes That Respond to the Second Messengers cGMP and cAMP"., Nature Structural Biology, vol. 6, No. 11, pp. 1062-1071, (1999).

Koizumi, M., et al., "Molecular Recognition of cAMP by an RNA Aptamer"., Biochemistry, vol. 39, No. 30, pp. 8983-8992, (2000).

Lato, S.M., et al., "In vitro selection of RNA lectins: Using combinatorial chemistry to interpret ribozyme evolution"., Chemistry & Biology, vol. 2, No. 5, pp. 291-303, (1995).

Lauhon, C.T., et al., "RNA aptamers that bind flavin and nicotinamide redox cofactors"., J. Am. Chem. Soc., vol. 117, No. 4, pp. 1246-1257, (1995).

Lee, M., et al., "A fiber-optic microarray biosensor using aptamers as receptors"., Analytical Biochemistry, vol. 282, pp. 142-146, (2000).

Lehman, N., et al., "Evolution in vitro of an RNA enzyme with altered metal dependence"., Nature, vol. 361, pp. 182-185, (1993).

Levy, M., et al., "ATP-Dependent Allosteric DNA Enzymes"., Chemistry & Biology, vol. 9, pp. 417-426, (2002).

Li, J., et al., "A highly sensitive and selective catalytic DNA biosensor for lead ions"., J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme"., Nucleic Acids Research, vol. 28, No. 2, pp. 481-488, (2000).

Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).

Li, Y., et al., "A catalytic DNA for porphyrin metallation"., Nature Structural Biology, vol. 3, No. 9, pp. 743-747, (1996).

Li, Y., et al., "Capping DNA with DNA"., Biochemistry, vol. 19, No. 11, pp. 3106-3114, (2000).

Li, Y., et al., "Deoxyribozymes: new players in the ancient game of biocatalysis"., Current Opinion in Structural Biology, vol. 9, pp. 315-323, (1999).

Li, Y., et al., "Phosphorylating DNA with DNA"., Proc. Natl. Acad. Sci. USA, vol. 96, pp. 2746-2751, (1999).

Link, S., et al., "Alloy formation of gold-silver nanoparticles and the dependence of the plasmon absorption on their composition"., J. Phys. Chem. B, vol. 103, No. 18, pp. 3529-3533, (1999).

Liu, J., et al., "A colorimetric lead biosensor using DNAzyme-directed assembly of gold nanoparticles"., J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).

Liu, J., et al., "Adenosine-dependent assembly of aptazyme-functinalized gold nanoparticles and its application as a colorimetric biosensor"., Analytical Chemistry, vol. 76, No. 6, pp. 1627-1632, (2004).

Liu, J., et al., "Colorimetric biosensors based on DNAzyme-assembled gold nanoparticles"., Journal of Fluorescence, vol. 14, No. 4, pp. 343-354, (2004).

Liu, X., et al., "A fiber-optic evanescent wave DNA biosensor based on novel molecular beacons"., Analytical Chemistry, vol. 71, No. 22, pp. 5054-5059, (1999).

Lohse, P.A., et al., "Ribozyme-catalysed amino-acid transfer reactions"., Nature, vol. 381, pp. 442-444, (1996).

Lorsch, J.R., et al., "In vitro evolution of new ribozymes with polynucleotide kinase activity"., Nature, vol. 371, pp. 31-36, (1994).

Lorsch, J.R., et al., "In vitro selection of RNA aptamers specific for cyanocobalamin"., Biochemistry, vol. 33, No. 4, pp. 973-982, (1994).

Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).

Lu, Y., "New transition-metal-dependent DNAzymes as efficient endonucleases and as selective metal biosensors"., Chem. Eur. J., vol. 8, No. 20, pp. 4589-4596, (2002).

Lu, Y., et al., "New fluorescent and colorimetric DNAzyme biosensors for metal ions", Journal of Inorganic Biochemistry, vol. 96, issue 1, pp. 30, Abstract of the 11th International Conference on Biological Inorganic Chemistry; (Jul. 15, 2003).

Majerfeld, I., et al., "An RNA pocket for an aliphatic hydrophobe"., Structural Biology, vol. 1, No. 5, pp. 287-292, (1994).

Majerfeld, I., et al., "Isoleucine:RNA sites with associated coding sequences"., RNA, vol. 4, pp. 471-478, (1998).

Mannironi, C., et al., "In vitro selection of dopamine RNA ligands"., Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants"., Langmuir, vol. 3, No. 6, pp. 1034-1044, (1987).

Marsh, T.C., et al., "A new DNA nanostructure, the G-wire, imaged by scanning probe microscopy"., Nucleic Acids Research, vol. 23, No. 4, pp. 696-700, (1995).

Matteucci, M.D., et al., "Synthesis of Deoxyoligonucleotides on a polymer support"., J. Am. Chem. Soc., vol. 103, No. 11, pp. 3185-3191. (1981).

Mirkin, C.A., et al., "A DNA-based method for rationally assembling nanoparticles into macroscopic materials"., Nature, vol. 382, pp. 607-609, (1996).

Mirkin, S.M., et al., "H-DNA and related structures"., Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin"., Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer"., Chem. Commun., pp. 555-557, (1996).

Nissen, P., et al., "The structural basis of ribosome activity in peptide bond synthesis"., Science, vol. 289, pp. 920-930, (2000).

Nolte, A., et al., "Mirror-design of L-oligonucleotide ligands binding to L-arginine"., Nature Biotechnology, vol. 14, pp. 1116-1119, (1996).

Nutiu, R., et al., "Structure-switching signaling aptamers"., J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry"., Analytical Chemistry, vol. 69, No. 13, pp. 2438-2443, (1997).

Oehme, I., et al., "Optical sensors for determination of heavy metal ions"., Mikrochim. Acta, vol. 126, pp. 177-192, (1997).

Ohmichi, T., et al., "Effect of substrate RNA sequence on the cleavage reaction by a short ribozyme".. Nucleic Acids Research, vol. 26, No. 24, pp. 5655-5661, (1998).

Okazawa, A., et al., "In vitro selection of hematoporphyrin binding DNA aptamers"., Bioorganic & Medicinal Chemistry, Letters 10, pp. 2653-2656, (2000).

Ota, N., et al., "Effects of helical structures formed by the binding arms of DNAzymes and their substrates on catalytic activity"., Nucleic Acids Research, vol. 26, No. 14, pp. 3385-3391, (1998).

Pan, T., et al., "A small metalloribozyme with a two-step mechanism".., Nature, vol. 358, pp. 560-563, (1992).

Pan, T., et al., "In vitro selection of RNAs that undergo autolytic cleavage with $Pb^{2+}$"., Biochemistry, vol. 31, No. 16, pp. 3887-3895, (1992).

Pan, T., et al., "Properties of an in vitro selected $Pb^{2+}$ cleavage motif"., Biochemistry, vol. 33, No. 32, pp. 9561-9565, (1994).

Pavlov, V., et al., "Aptamer-functionalized au nanoparticles for the amplified optical detection of thrombin"., J. Am. Chem. Soc., vol. 126, No. 38, pp. 11768-11769, (2004).

Pearce, D.A., et al., "Peptidyl chemosensors incorporating a FRET mechanism for detection of Ni(II)"., Bioorganic & Medicinal Chemistry, Letters 8, pp. 1963-1968, (1998).

Pease, A.C., et al., "Light-generated oligonucleotide arrays for rapid DNA sequence analysis"., Proc. Natl. Acad. Sci. USA, vol. 91, pp. 5022-5026, (1994).

Piccirilli, J.A., et al., "Aminoacyl esterase activity of the tetrahymena ribozyme"., Science, New Series, vol. 256, issue 5062, pp. 1420-1424, (1992).

Pley, H.W., et al., "Three-dimensional structure of a hammerhead ribozyme"., Nature, vol. 372, pp. 68-74, (1994).

Potyrailo, R.A., et al., "Adapting selected nucleic acid ligands (aptamers) to biosensors"., Analytical Chemistry, vol. 70, No. 16, pp. 3419-3425, (1998).

Prudent, J.R., et al., "Expanding the scope of RNA catalysis"., Science, New Series, vol. 264, issue 5167, pp. 1924-1927, (1994).

Rabinowitz, M., et al., "Home refinishing, lead paint, and infant blood lead levels"., American Journal of Public Health, vol. 75, No. 4, pp. 403-404, (1985).

Rajendran, M., et al., "Selecting nucleic acids for biosensor applications"., Combinatorial Chemistry and High Throughput Screening, vol. 5, No. 4, pp. 263-270, (2002).

Rakow, N.A., et al., "A colorimetric sensor array for odour visualization"., Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).

Robertson, M.P., et al., "Design and optimization of effector-activated ribozyme ligases"., Nucleic Acids Research, vol. 28, No. 8, pp. 1751-1759, (2000).

Robertson, M.P., et al., "In vitro selection of an allosteric ribozyme that transduces analytes to amplicons"., Nature Biotechnology, vol. 17, pp. 62-66, (1999).

Roth, A., et al., "An amino acid as a cofactor for a catalytic polynucleotide"., Proc. Natl. Acad. Sci. USA, vol. 95, pp. 6027-6031, (1998).

Rurack, K., et al., "A selective and sensitive fluoroionophore for $Hg^{II}$, $Ag^{I}$, and $Cu^{II}$ with virtually decoupled fluorophore and receptor units"., J. Am. Chem. Soc., vol. 122, No. 5, pp. 968-969, (2000).

Rusconi, C.P., et al., "RNA aptamers as reversible antagonists of coagulation factor Ixa"., Nature, vol. 419, pp. 90-94. (2002).

Sabanayagam, C.R., et al., "Oligonucleotide immobilization on micropatterened streptavidin surfaces"., Nucleic Acids Research, vol. 28, No. 8, e33, pp. i-iv, (2000).

Santoro, S.W., et al., "Mechanism and utility of an RNA-cleaving DNA enzyme"., Biochemistry, vol. 37, No. 38, pp. 13330-13342, (1998).

Santoro, S.W., et al., "A general purpose RNA-cleaving DNA enzyme"., Proc. Natl. Acad. Sci. USA, vol. 94, pp. 4262-4266, (1997).

Santoro, S.W., et al., "RNA Cleavage by a DNA Enzyme with Extended Chemical Functionality"., J. Am. Chem. Soc., vol. 122, No. 11, pp. 2433-2439, (2000).

Sassanfar, M., et al., "An RNA motif that binds ATP"., Nature, vol. 364, pp. 550-553, (1993).

Schwartz, J., et al., "The risk of lead toxicity in homes with lead paint hazard"., Environmental Research, vol. 54, No. 1, pp. 1-7, (1991).

Scott, W.G., et al., "The crystal structure of an all-RNA hammerhead ribozyme: A proposed mechanism for RNA catalytic cleavage"., Cell, vol. 81, pp. 991-1002, (1995).

Seeman, N.C., et al., "Synthetic DNA knots and catenanes"., New Journal of Chemistry, vol. 17, pp. 739-755, (1993).

Seetharaman, S., et al., "Immobilized RNA switches for the analysis of complex chemical and biological mixtures"., Nature Biotechnology, vol. 19, pp. 336-341, (2001).

Sen, D., et al., "DNA enzymes"., Current Opinion in Chemical Biology, vol. 2, pp. 680-687, (1998).

Shaiu, W-L., et al., "Atomic force microscopy of oriented linear DNA molecules labeled with 5nm gold spheres"., Nucleic Acids Research, vol. 21, No. 1, pp. 99-103, (1993).

Shaw, S.Y., et al., "Knotting of a DNA chain during ring closure"., Science, New Series, vol. 260, issue 5107, pp. 533-536, (1993).

Shekhtman, E.M., et al., "Stereostructure of replicative DNA catenanes from eukaryotic cells"., New Journal of Chemistry, vol. 17, pp. 757-763, (1993).

Sigurdsson, S.T., et al., "Small ribozymes"., RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time"., Biotechniques, vol. 29, No. 2, pp. 344-351, (2000).

Smith, F.W., et al., "Quadruplex structure of oxytricha telomeric DNA oligonucleotides"., Nature, vol. 356, pp. 164-168, (1992).

Smith, J.O., et al., "Molecular recognition of PNA-containing hybrids: Spontaneous assembly of helical cyanine dye aggregates on PNA templates"., J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concetration"., J. Am. Chem. Soc., vol. 104, No. 14, pp. 3937-3945, (1982).

Soukup, G.A., et al., "Allosteric nucleic acid catalysts"., Current Opinion in Structural Biology, vol. 10, pp. 318-325, (2000).

Stage-Zimmermann, T.K., et al., "Hammerhead ribozyme kinetics"., RNA, vol. 4, pp. 875-889, (1998).

Stojanovic, M.N., et al., "Aptamer-based colorimetric probe for cocaine"., J. Am. Chem. Soc., vol. 124, No. 33, pp. 9678-9679, (2002).

Stojanovic, M.N., et al., "Aptamer-based folding fluorescent sensor for cocaine"., Journal of the American Chemical Society, vol. 123, No. 21, pp. 4928-4931, (2001).

Stojanovic, M.N., et al., "Fluorescent sensors based on aptamer self-assembly"., Journal of the American Chemical Soceity, vol. 122, No. 46, pp. 11547-11548, (2000).

Storhoff, J.J., et al., "One-pot colorimetric differentiation of polynucleotides with single base imperfections using gold nanoparticle probes"., Journal of the American Chemical Society, vol. 120, No. 9, pp. 1959-1964, (1998).

Sun, L.Q., et al., "Catalytic nucleic acids: From lab to applications"., Pharmacological Reviews, vol. 52, pp. 325-347, (2000).

Tang, J., et al., "Rational design of allosteric ribozymes"., Chemistry & Biology, vol. 4, No. 6, pp. 453-459, (1997).

Tang, J., et al., "Structural diversity of self-cleaving ribozymes"., Proc. Natl. Acad. Sci. USA, vol. 97, No. 11, pp. 5784-5789, (2000).

Tanner, N.K., "Biochemistry of hepatitis delta virus catalytic RNAs"., Ribozymes in the Gene Therapy of Cancer, Chapter 3, pp. 23-38, (1998).

Tao, J., et al., "Arginine-Binding RNAs Resembling TAR Identified by in Vitro Selection"., Biochemistry, vol. 35, No. 7, pp. 2229-2238, (1996).

Tarasow, T.M., et al., "RNA-catalysed carbon-carbon bond formation"., Nature, vol. 389, pp. 54-57, (1997).

Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy"., Journal of Colloid and Interface Science, vol. 49, No. 3, pp. 410-421, (1974).

Travascio, P., et al., "A ribozyme and a catalytic DNA with peroxidase activity: active sites versus cofactor-binding sites"., Chemistry & Biology, vol. 6, No. 11, pp. 779-787, (1999).

Tsang, J., et al., "In vitro evolution of randomized riboyzmes"., Methods in Enzymology, vol. 267, pp. 410-426, (1996).

Tuerk, C., et al., "RNA pseudoknots that inhibit human immunodeficiency virus type 1 reverse transcriptase"., Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase"., Science, New Series, vol. 249, issue 4968, pp. 505-510, (1990).

Tyagi, S., et al., "Molecular Beacons: Probes that fluoresce upon hybridization"., Nature Biotechnology, vol. 14, pp. 303-308, (1996).

Tyagi, S., et al., "Multicolor molecular beacons for allele discrimination"., Nature Biotechnology, vol. 16, pp. 49-53, (1998).

Uphoff, K.W., et al., "In vitro selection of aptamers: the dearth of pure reason"., Current Opinion in Structural Biology, vol. 6, pp. 281-288, (1996).

Vaish, N.K., et al., "In vitro selection of a purine nucleotide-specific hammerhead-like ribozyme"., Proc. Natl. Acad. Sci. USA, vol. 95, pp. 2158-2162, (1998).

Valadkhan, S., et al., "Splicing-related catalysis by protein-free snRNAs"., Nature, vol. 413, pp. 701-707, (2001).

Vianini, E., et al., "In vitro selection of DNA aptamers that bind L-tyrosinamide"., Bioorganic & Medicinal Chemistry, vol. 9, pp. 2543-2548, (2001).

Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA motif for neomycin recognition"., Chemsitry & Biology, vol. 2, No. 8, pp. 543-552, (1995).

Wallis, M.G., et al., "In vitro selection of a viomycin-binding RNA pseudoknot"., Chemistry & Biology, vol. 4, No. 5, pp. 357-366, (1997).

Walter, F., et al., "Folding of the four-way RNA junction of the hairpin ribozyme"., Biochemistry, vol. 37, No. 50, pp. 17629-17636, (1998).

Walter, N.G., et al., "The hairpin ribozyme: structure, assembly and catalysis"., Current Opinion in Chemical Biology, vol. 2, pp. 24-30, (1998).

Wang, D.Y., et al., "A general strategy for effector-mediated control of RNA-cleaving ribozymes and DNA enzymes"., J. Mol. Biol., vol. 318, pp. 33-43, (2002).

Wang, F., et al., "Sphingosine-1-phosphate Inhibits Motility of Human Breast Cancer Cells Independently of Cell Surface Receptors"., Cancer Research, vol. 59, pp. 6185-6191, (1999).

Wang, J., "Survey and Summary: From DNA biosensors to gene chips"., Nucleic Acids Research, vol. 28, No. 16, pp. 3011-3016, (2000).

Wang, K.Y., et al., "A DNA aptamer which binds to and inhibits thrombin exhibits a new structural motif for DNA"., Biochemistry, vol. 32, No. 8, pp. 1899-1904, (1993).

Wang, Y., et al., "Assembly and characterization of five-arm and six-arm DNA branched junctions"., Biochemistry, vol. 30, pp. 5667-5674, (1991).

Wang, Y., et al., "RNA molecules that specifically and stoichiometrically bind aminoglycoside antibiotics with high affinities"., Biochemistry, vol. 35, No. 38, pp. 12338-12346, (1996).

Wecker, M., et al., "In vitro selection of a novel catalytic RNA: characterization of a sulfur alkylation reaction and interaction with a small peptide"., RNA, vol. 2, pp. 982-994, (1996).

Wedekind, J.E., et al., "Crystal structure of a lead-dependent ribozyme revealing metal binding sites relevant to catalysis" ., Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and allo site ion regulation"., Biochemistry, vol. 42, No. 32, pp. 9554-9563, (2003).

Wells, R.D., "Unusual DNA structures"., Journal of Biological Chemistry, vol. 263, No. 3, pp. 1095-1098, (1988).

Werstuck, G., et al., "Controlling gene expression in living cells through small molecule-RNA interactions"., Science, vol. 282, pp. 296-298, (1998).

Whitesides, G.M., et al., "Self-assembled mohnolayers and lithography"., Proceedings of the Robert A. Welch Foundation 39th Conference On Chemical Research on Naophase Chemistry, pp. 109-121, Houston, TX, Oct. 23-24, 1995.
Wiegand, T.W., et al., "Selection of RNA amide synthases"., Chemistry & Biology, vol. 4, No. 9, pp. 675-683, (1997).
Williams, K.P., et al., "Bioactive and nuclease-resistant L-DNA ligand of vasopressin"., Proc. Natl. Acad. Sci. USA, vol. 94, pp. 11285-11290, (1997).
Williams, K.P., et al., "Selection of novel $Mg^{2+}$-dependent self-cleaving ribozymes" The EMBO Journal, vol. 14, No. 18, pp. 4551-4557, (1995).
Wilson, C., et al., "Functional requirements for specific ligand recognition by a biotin-binding RNA Pseudoknot"., Biochemistry, vol. 37, No. 41, pp. 14410-14419, (1998).
Wilson, C., et al., "In vitro evolution of a self-alkylating ribozyme"., Nature, vol. 374, pp. 777-782, (1995).
Wilson, C., et al., "Isolation of a fluorophore-specific DNA aptamer with weak redox activity"., Chemistry & Biology, vol. 5, No. 11, pp. 609-617, (1998).
Wilson, D.S., et al., "In vitro selection of functional nucleic acids"., Annu. Rev. Biochem. vol. 68, pp. 611-647, (1999).
Winkler, J.D., et al., "Photodynamic Fluorescent Metal Ion Sensors with Parts per Billion Sensitivity"., J. Am. Chem. Soc., vol. 120, No. 13, pp. 3237-3242, (1998).
Xia, P., et al., "Activation of Sphingosine Kinase by Tumor Necrosis Factor-α Inhibits Apoptosis in Human Endothelial Cells"., Journal of Biological Chemsitry, vol. 274, No. 48, pp. 34499-34505, (1999).
Yang, Q., et al., "DNA ligands that bind tightly and selectively to cellobiose"., Proc. Natl. Acad. Sci. USA, vol. 95, pp. 5462-5467, (1998).
Yurke, B., et al., "A DNA-fuelled molecular machine made of DNA"., Nature, vol. 406, pp. 605-608, (2000).
Zhang, B., et al., "Peptide bond formation by in vitro selected ribozymes"., Nature, vol. 390, pp. 96-100, (1997).
Zhang, P., et al., "Design of a molecular beacon DNA probe with two fluorophores"., Angewandte Chemie International Edition, vol. 40, No. 2, pp. 402-405, (2001).
Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).
Zimmerman, J.M., et al., "In vivo selection of spectinomycin-binding RNAs"., Nucleic Acids Research, vol. 30, No. 24, pp. 5425-5435, (2002).
Zimmermann, G.R., et al., "Molecular interactions and metal binding in the theophylline-binding core of an RNA aptamer"., RNA, vol. 6, pp. 659-667, (2000).
Aggarwal, S.K., et al., "Determination of lead in urine and whole blood by stable isotope dilution gas chromatography-mass spectrometry"., Clinical Chemistry, vol. 40, No. 8, pp. 1494-1502, (1994).
Alivisatos, A.P., et al., "Organization of "nanocrystal molecules" using DNA"., Nature, vol. 382, pp. 609-611, (1996).
Bannon, D.I., et al., "Graphite furnace atomic absorption spectroscopic measurement of blood lead in matrix-matched standards"., Clinical Chemistry, vol. 40, No. 9, pp. 1730-1734, (1994).
Berens, C., et al., "A tetracycline-binding RNA aptamer"., Bioorganic & Medicinal Chemistry, vol. 9, pp. 2549-2556, (2001).
Bowins, R.J., et al., "Electrothermal isotope dilution inductively coupled plasma mass spectrometry method for the determination of sub-ng-$ml^1$ levels of lead in human plasma"., Journal of Analytical Atomic Spectrometry, vol. 9, pp. 1233-1236, (1994).
Breaker, R.R., "DNA aptamers and DNA enzymes" Current Opinion in Chemical Biology, vol. 1, pp. 26-31, (1997).
Brust, M., et al., "Novel gold-dithiol nano-networks with non-metallic electronic properties"., Advanced Materials, vol. 7, No. 9, pp. 795-797, (1995).
Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).
Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).
Chartrand, P., et al., "Effect of structural modifications on the activity of the leadzyme"., Biochemistry, vol. 36, No. 11, pp. 3145-3150, (1997).
Chen, J., et al., "Synthesis from DNA of a molecule with the connectivity of a cube"., Nature, vol. 350, pp. 631-633, (1991).
Chen, C-T., et al., "A highly selective fluorescent chemosensor for lead ions"., J. Am. Chem. Soc., vol. 124, pp. 6246-6247, (2002).
Chinnapen, D.J.F., et al., "Hemin-stimulated docking of cytochrome c to a hemin-DNA aptamer complex"., Biochemistry, vol. 41, No. 16, pp. 5202-5212, (2002).
Dubois, L.H., et al., "Synthesis, structure, and properties of model organic surfaces"., Annu. Rev. Phys. Chem., vol. 43, pp. 437-463, (1992).
Feldman, B.J., et al., "Determination of lead in blood by square wave anodic stripping voltammetry at a carbon disk ultramicroelectrode"., Analytical Chemistry, vol. 66, No. 13, pp. 1983-1987, (1994).
Ferguson, A., et al., "A novel strategy for selection of allosteric ribozymes yields riboreporter™ sensors for caffeine and aspartame"., Nucleic Acids Research, vol. 32, No. 5, pp. 1756-1766, (2004).
Granadillo, V.A., et al., "The influence of the blood levels of lead, aluminum and vanadium upon the arterial hypertension"., Clinica Chimica Acta, vol. 233, pp. 47-59, (1995).
Hartig, J.S., et al., "Reporter ribozymes for real-time analysis of domain-specific interactions in biomolecules: HIV-1 reverse transcriptase and the primer-template complex"., Angew. Chem. Int. Ed., vol. 41, No. 22, pp. 4263-4266, (2002).
He, X-x., et al., "Bioconjugated nanoparticles for DNA protection from cleavage"., J. Am. Chem. Soc., vol. 125, No. 24, pp. 7168-7169, (2003).
Hock, B., "Antibodies for immunosensors, A review"., Analytica Chimca Acta, vol. 347, pp. 177-186, (1997).
Hoogstraten, C.G., et al., "NMR solution structure of the lead-dependent ribozyme: Evidence for dynamics in RNA catalysis"., J. Mol. Biol., vol. 284, pp. 337-350, (1998).
Iqbal, S.S., et al., "A review of molecular recognition technologies for detection of biological threat agents"., Biosensors & Bioelectronics, vol. 15, pp. 549-578, (2000).
Jagner, D., et al., "Determination of lead in microliter amounts of whole blood by stripping potentiometry"., Electroanalysis, vol. 6, pp. 285-291, (1994).
Jin., R., et al., "What controls the melting properties of DNA-linked gold nanoparticle assemblies?"., J. Am. Chem. Soc., vol. 125, No. 6, pp. 1643-1654, (2003).
Katahira, M., et al., "Two metal-binding sites in a lead ribozyme bound to competitively by $Pb^{2+}$ and $Mg^{2+}$: Induced structural changes as revealed by NMR"., European Journal of Biochemistry, vol. 255, pp. 727-733, (1998).
Khan, R., et al., "Interaction of retroviral nucleocapsid proteins with transfer $RNA^{phe}$: a lead ribozyme and $^1H$ NMR study"., Nucleic Acids Research, vol. 24, No. 18, pp. 3568-3575, (1996).
Khosraviani, M., et al., "Detection of heavy metals by immunoassay: Optimization and validation of a rapid, portable assay for ionic cadmium"., Environ. Sci. Technol., vol. 32, No. 1, pp. 137-142, (1998).
Kim, M.H., et al., "Activation and repression of the activity of a lead ribozyme by the combination of $Pb^{2+}$ and $Mg^{2+1}$"., J. Biochem., vol. 122, No. 5, pp. 1062-1067, (1997).
Koizumi, M., et al., "Allosteric ribozymes sensitive to the second messengers cAMP and cGMP"., Nucleic Acids Symposium Series, No. 42, pp. 275-276, (1999).
Kruger, K., et al., "Self-splicing RNA: autoexcision and autocyclization of the ribosomal RNA intervening sequence of the Tetrahymena"., Cell, vol. 31, pp. 147-157, (1982).
Lebruska, L.L., "Selection and Characterization of an RNA Decoy for Transcription Factor NF-$_к$B"., Biochemistry, vol. 38, No. 10, pp. 3168-3174, (1999).
Lee, S-W., et al., "Ordering of quantum dots using genetically engineered viruses"., Science, vol. 296, pp. 892-895, (2002).

Legault, P., et al., "Order, dynamics and metal-binding in the lead-dependent ribozyme"., J. Mol. Biol., vol. 284, pp. 325-335, (1998).

Lemieux, S., et al., "Modeling active RNA structures using the intersection of conformational space: application to the lead-activated ribozyme"., RNA, vol. 4, pp. 739-749, (1998).

Liu, H-W., et al., "Determination of cadmium, mercury and lead in seawater by electrothermal vaporization isotope dilution inductively coupled plasma mass spectrometry,"., Spectrochimica Acta Part B Atomic Spectroscopy 54, pp. 1367-1375, (1999).

Liu, J., et al., "Highly dispersible molecular sieve carbon nanoparticles"., Chem. Mater., vol. 16, No. 22, pp. 4205-4207, (2004).

Liu, Z., et al., "Assemblage of signaling DNA enzymes with intriguing metal-ion specificities and pH dependences"., J. Am. Chem. Soc., vol. 125, No. 25, pp. 7539-7545, (2003).

Marcus, A.H., et al., "Estimating the contribution of lead based paint to soil lead, dust lead, and childhood blood lead"., American Society for Testing and Materials Spec. STP 1226, pp. 12-23, (1995).

Mecklenburg, M., et al., "A strategy for the broad range detection of compounds with affinity for nucleic acids"., Analytica Chimica Acta, vol. 347, pp. 79-86, (1997).

Mei, S.H.J., et al., "an efficient RNA-cleaving DNA enzyme that synchronizes catalysis with fluorescence signaling"., J. Am. Chem. Soc., vol. 125, No. 2, pp. 412-420, (2003).

Meli, M., et al., "Adenine-aptamer complexes: A bipartite RNA site that binds the adenine nucleic base"., The Journal of Biological Chemistry, vol. 277, No. 3, pp. 2104-2111, (2002).

Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).

Nazarenko, I.A., et al., "A closed tube format for amplification and detection of DNA based on energy transfer"., Nucleic Acids Research, vol. 26, No. 12, pp. 2516-2521, (1997).

Nazarenko, I.A., et al., "Defining a Smaller RNA Substrate for Elongation Factor Tu"., Biochemistry, vol. 34, No. 8, pp. 2545-2552, (1995).

Niemeyer, C.M., "Nanoparticles, proteins, and nucleic acids: Biotechnology meets materials science"., Angew. Chem. Int. Edition, vol. 40, pp. 4128-4158, (2001).

Nieuwlandt, D., et al., "In Vitro Selection of RNA Ligands to Substance P"., Biochemistry, vol. 34, No. 16, pp. 5651-5659, (1995).

Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).

Pan, W., et al., "Isolation of virus-neutralizing RNAs from a large pool of random sequences"., Proc. Natl. Acad. Sci. USA, vol. 92, pp. 11509-11513, (1995).

Park, S-J., et al., "Array-based electrical detection of DNA with nanoparticle probes"., Science, vol. 295, pp. 1503-1506, (2002).

Parsons, P.J., et al., "A rapid Zeeman graphite furnace atomic absorption spectrometric method for the determination of lead in blood"., Spectrochimica Acta, vol. 48B, No. 6/7, pp. 925-939, (1993).

Pavlov, A.R., et al., "Determination of lead in environmental water samples by a rapid and portable immunoassay"., ANYL, Book of Abstracts, 219th ACS National Meeting, San Diego, CA, Mar. 26-30, 2000.

Qiao, H., et al., "Transferability of blood lead determinations by furnace atomic absorption spectrophotometry and continuum background correction"., Clinical Chemistry, vol. 41, No. 10, pp. 1451-1454, (1995).

Roychowdhury-Saha, M., et al., "Flavin Recognition by an RNA Aptamer Targeted toward FAD"., Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).

Scott, W.G., "RNA catalysis"., Current Opinion in Structural Biology, vol. 8, pp. 720-726, (1998).

Seeman, N.C., et al., "Emulating biology: Building nanostructures from the bottom up"., Proc. Natl. Acad. Sci., vol. 99, suppl. 2, pp. 6451-6455, (2002).

Seeman, N.C., "DNA in a material world"., Nature, vol. 421, pp. 427-431, (2003).

Soukup, G.A., et al., "Engineering precision RNA molecular switches"., Proc. Natl. Acad. Sci. USA, vol. 96, pp. 3584-3589, (1999).

Srisawat, C., et al., "Sephadex-binding RNA ligands: rapid affinity purification of RNA from complex RNA mixtures"., Nucleic Acids Research, vol. 29, No. 2 e4, pp. 1-5, (2001).

Storhoff, J.J., et al., "Programmed materials synthesis with DNA"., Chem. Rev., vol. 99, No. 7, pp. 1849-1862, (1999).

Storhoff, J.J., et al., "What Controls the Optical Properties of DNA-Linked gold Nanoparticle Assemblies?"., J. Am. Chem. Soc., vol. 122, No. 19, pp. 4640-4650, (2000).

Streicher, B., et al., "Lead cleavage site in the core structure of group I intron-RNA"., Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions"., FEBS Letters, vol. 393, pp. 97-100, (1996).

Tahan, J.E., et al., "Electrothermal atomic absorption spectrometric determination of Al, Cu, Ge, Pb, V and Zn in clinical samples and in certified environmental reference materials"., Analytica Chimica Acta, vol. 295, pp. 187-197, (1994).

Takagi, Y., et al., "Survey and Summary: Recent advances in the elucidation of the mechanisms of action of ribozymes"., Nucleic Acids Research, vol. 29, No. 9, pp. 1815-1834, (2001).

Telting-Diaz, M., et al., "Mass-produced ionophore-based fluorescent microspheres for trace level determination of lead ions"., Analytical Chemistry, vol. 74, No. 20, pp. 5251-5256, (2002).

Tsien, R.Y., "Fluorescent and photochemical probes of dynamic biochemical signals inside living cells"., Fluorescent Chemosensors for Ion and Molecule Recognition, (ed. Czarnik, A. W.), chapter 9, pp. 130-146, American Chemical Society, (1993).

Tyagi, S., et al., "Wavelength-shifting molecular beacons"., Nature Biotechnology, vol. 18, pp. 1191-1196, (2000).

Ueyama, H., "A novel potassium sensing in aqueous media with a synthetic oligonucleotide derivative. Fluorescence resonance energy transfer associated with guanine quartet-potassium ion complex formation"., J. Am. Chem. Soc., vol. 124, No. 48, pp. 14286-14287, (2002).

Whaley, S.R., et al., "Selection of peptides with semiconductor binding specificity for directed nanocrystal assembly"., Nature, vol. 405, pp. 665-668, (2000).

Wiegand, T.W., et al., "High-affinity oligonucleotide ligands to human IgE inhibit binding to Fc epsilon receptor I"., The Journal of Immunology, vol. 157, pp. 221-230, (1996).

Wittmann, C., et al., "Microbial and Enzyme sensors for environmental monitoring"., Handbook of Biosensors and Electronic Noses: Medicine, Food, and the Environment, pp. 299-332, (1997).

Yan, H., et al., "DNA-Templated self-assembly of protein arrays and highly conductive nanowires"., Science, vol. 301, pp. 1882-1884, (2003).

International Search Report dated Nov. 21, 2005 for corresponding PCT application No. PCT/US2005/001060.

Supplemental International Search Report dated Jan. 10, 2006 for corresponding PCT application No. PCT/US2005/001060.

Liu, J., et al., "Size control, metal substitution, and catalytic application of cryptomelane nanomaterials prepared using crosslinking reagents"., Chem. Mater., vol. 16, No. 2, pp. 276-285, (2004).

Cake, K.M., et al., "Partition of circulating lead between serum and red cells is different for internal and external sources of lead"., American Journal of Industrial Medicine, vol. 29, pp. 440-445, (1996).

English Translation of Yang, Y., et al., "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).

* cited by examiner

Zn-DNA

5'- CTGCAGAATTCTAATACGACTCACTATAGGAAGAGATGGCGAC

Class I (used for reselection)
5,6,7,9,21,25,29,43,47
       ATCTC TTTTGTCAGCGACTCGAAATAGTGTGTTGAAGCAGCTCTA GTGAC

Class II
2,10,17,20,24,31,37,39
       AGCCA -TAGTTCTACCAGCGGTTCGAAATAGTGAAGTGTTCGTGA CTATC
3    GGCCA -TAGTTCTACCAGCGGTTCGAAATAGTGAAATGTTCGTGA CTATC
4    GCCAGATTAGTTCTACCAGCGGTTCGAAATAGTGAAATGTTCGTGA CTATC

Class III
15,18,19,34,35,38,50
       ATCTC CAAAGATGCCAGCATGCTATTCTCCGAGCCGGTCGAAATA GTGAC
14  ATCTC CAAAGATGCCTGCATGCTATTCTCCGAGCCGGTCGAAATA GTGAC

Unclassified
36  ATCTC GTCTCCGAGCCGGTCGAAATAGTCAGGTGTTTCTATTCGG GTGAC
40  ATCAC CTTCTCCGAGCCGGTCGAAATAGTAGTTTTTAGTATATCT GTGAC
42  ATCTC AGGTGTTGGCTGCTCTCGCGGTGGCGAGAGGTAGGGTGAT GTGAC

GGTAAGCTTGGCAC-3'

FIG. 2

Co-DNA

5'-CTGCAGAATTCTAATACGACGCACTATAGGAAGAGATGGCGAC

Class I (used for reselection)
18,15,34
     ATCTC TTGTATTAGCTACACTGTTAGTGGATCGGGTCTAATCTCG ·GTGAC
1    GTCTC TTGTATTAGCTACACTGTTAGTGGATCGGGTCTAATCTCG GTGAC
25  ATCTC CTGTATTAGCTACACTGTTAGTGGATCGGGTCTAATCTCG GTGAC
16  ATCTC TTGTATTAGCTACACTGTTAGTGGGAACGTTATCAT-TCG GTGAC

Class II
2,4,7,23,26
     ATCTC TTGACCCAAGAAGGGGTGTCAATCTAATCCGT CAACCATG
8   ATCTC TTGACCCAAGAAGGGGTGTCAATCAAATCCGT CAACCATG
17  ATCTC TTGACCCAAGAAGGGGTGTCAATCTAATCCGTACAACCATG ACGGTAAG
27  ATCTC TTGACCCAAGAAGGGGTGTCAATCTAATCCGT CAAGGATG  CGGTAAG

Class III
5   ATCTC AGGTGTTGGCTGCTCCCGCGGTGGCGGGAGGTAGGGTGAT GTGAC
11  ATCTC AGGTGTTGGCATCTCCCGCGGTGGCGAGAGGTAGGGTGAT GTGAC
6   ATCTC AGGTGTTGGCTGCTCTCGCGGTGGCGAGAGGTAGGGTCAT GTGAC

Unclassified
21  ATCTC GCAGTCGAAGCTTCACTGTTAGTGCGGACGGGTAGACTTC GTGAC
29  ATTTC TTCTGAATCCTCAATGTTAGTGGACCTAGTCGTAGTCGAT GTGAC
12  ATCTC GGAGCCAGTTAGCATAATCTTCTGAATCCTCAATGTTAGT GTGAC
10  ATCTC GGTGTTGGCTGGATAGAGCCGGTAGGCCCTATCGTAGGGT GTGAC
1   GTCTC TTTTGTCCGCGACTCGAAATAGTGTGTTGAAGCAGCTCTA GTGAC
28  AGCCA TAGTTCTACCAGCGGTTCGAAATAGTGAAGTGTTCGTGACTATCG GTAA

GGTAAGCTTGGCAC-3'

FIG. 3

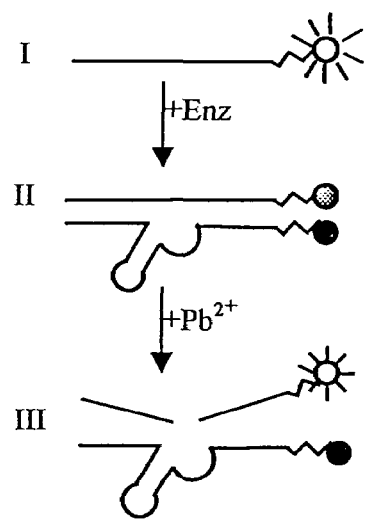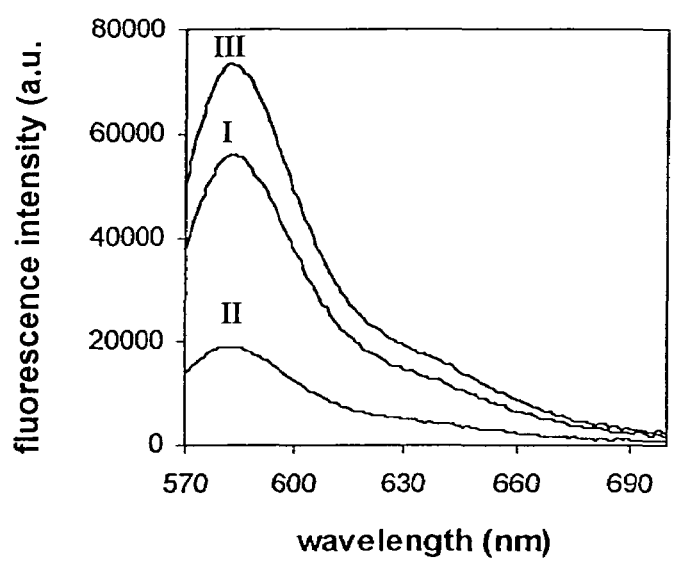
FIG. 8

HYPOTHETICAL SAMPLE RESULT

SEQUENCE LISTING

```
<160> NUMBER OF SEQ ID NOS: 88

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:
      Trans-cleaving
      deoxyribozyme 17E

<400> SEQUENCE: 1
catctcttct ccgagccggt cgaaatagtg agt                              33
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate
<220> FEATURE:
<221> NAME/KEY: modified_base
<222> LOCATION: (10)
<223> OTHER INFORMATION: ribonucleotide base

<400> SEQUENCE: 2
actcactata ggaagagatg                                              20

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 3
gtgccaagct taccg                                                   15

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 4
ctgcagaatt ctaatacgac tcactatagg aagagatggc gac                    43

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Description of Combined DNA/RNA Molecule:
      Primer
<220> FEATURE:
<221> NAME/KEY: modified_base
<222> LOCATION: (28)
<223> OTHER INFORMATION: ribonucleotide base

<400> SEQUENCE: 5
gggacgaatt ctaatacgac tcactata                                     28

<210> SEQ ID NO 6
<211> LENGTH: 97
<212> TYPE: DNA
<213> ORGANISM: Artificial Sequence
<220> FEATURE:
<223> OTHER INFORMATION: Description of Artificial Sequence:
      Synthetic DNA Template
<220> FEATURE:
<221> NAME/KEY: modified_base
<222> LOCATION: (20)..(59)
<223> OTHER INFORMATION: variable nucleotides -continued

```
<400> SEQUENCE: 6
gtgccaagct taccgtcacn nnnnnnnnnn nnnnnnnnnn nnnnnnnnnn nnnnnnnnng      60
agatctcgcc atctcttcct atagtgagtc gtattag                               97

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Variant of
      deoxyribozyme named 17E1

<400> SEQUENCE: 7
catctctttt gtcagcgact cgaaatagtg agt                                   33

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      Synthetic Zn-DNA
<220> FEATURE:
<221> NAME/KEY: modified_base
<222> LOCATION: (2)..(4)
<223> OTHER INFORMATION: variable bases complementary to positions 8-10
<220> FEATURE:
<221> NAME/KEY: modified_base
<222> LOCATION: (8)..(10)
<223> OTHER INFORMATION: variable bases complementary to positions 2-4

<400> SEQUENCE: 8
tnnnagcnnn tcgaaatagt                                                  20

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:
      Synthetic Zn-DNA
      sequence
<220> FEATURE:
<221> NAME/KEY: modified_base
<222> LOCATION: (2)..(4)
<223> OTHER INFORMATION: variable bases complementary to positions 8-10
<220> FEATURE:
<221> NAME/KEY: modified_base
<222> LOCATION: (8)..(10)
<223> OTHER INFORMATION: variable bases complementary to positions 2-4

<400> SEQUENCE: 9
tnnnagcnnn acgaa                                                       15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Class II
      Co-DNA sequence

<400> SEQUENCE: 10
acccaagaag gggtg                                                       15

<210> SEQ ID NO 11
<211> LENGTH: 20
<212> TYPE: DNA
```

<213> ORGANISM: Artificial Sequence
<220> FEATURE:
<223> OTHER INFORMATION: Description of Artificial Sequence:
      Synthetic Rh-17DDS

<400> SEQUENCE: 11
actcactata ggaagagatg                                              20

<210> SEQ ID NO 12
<211> LENGTH: 97
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate
<220> FEATURE:
<221> NAME/KEY: modified_base
<222> LOCATION: (39)..(78)
<223> OTHER INFORMATION: variable nucleotides

<400> SEQUENCE: 12
ctaatacgac tcactatagg aagagatggc gacatctcnn nnnnnnnnn nnnnnnnnn    60 nnnnnnnnnn nnnnnnnngt gacggtaagc ttggcac                           97

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 13
ctgcagaatt ctaatacgac tcactatagg aagagatggc gac                    43

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 14
atctcttttg tcagcgactc gaaatagtgt gttgaagcag ctctagtgac             50

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 15
agccatagtt ctaccagcgg ttcgaaatag tgaagtgttc gtgactatc              49

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence:

Synthetic Zn-DNA

<400> SEQUENCE: 16
ggccatagtt ctaccagcgg ttcgaaatag tgaaatgttc gtgactatc         49

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 17
gccagattag ttctaccagc ggttcgaaat agtgaaatgt tcgtgactat c      51

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 18
atctccaaag atgccagcat gctattctcc gagccggtcg aaatagtgac         50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 19
atctccaaag atgcctgcat gctattctcc gagccggtcg aaatagtgac         50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 20
atctcgtctc cgagccggtc gaaatagtca ggtgtttcta ttcgggtgac         50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 21
atcaccttct ccgagccggt cgaaatagta gttttagta tatctgtgac          50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence:
      Synthetic Zn-DNA

```
<400> SEQUENCE: 22
atctcaggtg ttggctgctc tcgcggtggc gagaggtagg gtgatgtgac            50

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 23
ggtaagcttg gcac                                                   14

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 24
ctgcagaatt ctaatacgac gcactatagg aagagatggc gac                   43

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 25
atctcttgta ttagctacac tgttagtgga tcgggtctaa tctcggtgac            50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 26
gtctcttgta ttagctacac tgttagtgga tcgggtctaa tctcggtgac            50

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 27
atctcctgta ttagctacac tgttagtgga tcgggtctaa tctcggtgac            50

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence:
      Synthetic Co-DNA
```

-continued

```
<400> SEQUENCE: 28
atctcttgta ttagctacac tgttagtggg aacgttatca ttcggtgac            49

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 29
atctcttgac ccaagaaggg gtgtcaatct aatccgtcaa ccatg               45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 30
atctcttgac ccaagaaggg gtgtcaatca aatccgtcaa ccatg               45

<210> SEQ ID NO 31
<211> LENGTH: 54
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 31
atctcttgac ccaagaaggg gtgtcaatct aatccgtaca accatgacgg taag      54

<210> SEQ ID NO 32
<211> LENGTH: 52
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 32
atctcttgac ccaagaaggg gtgtcaatct aatccgtcaa ggatgcggta ag        52

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 33
atctcaggtg ttggctgctc ccgcggtggc gggaggtagg gtgatgtgac           50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 34
```
atctcaggtg ttggcatctc ccgcggtggc gagaggtagg gtgatgtgac        50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 35
atctcaggtg ttggctgctc tcgcggtggc gagaggtagg gtcatgtgac        50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 36
atctcgcagt cgaagcttca ctgttagtgc ggacgggtag acttcgtgac        50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 37
atttcttctg aatcctcaat gttagtggac ctagtcgtag tcgatgtgac        50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 38
atctcggagc cagttagcat aatcttctga atcctcaatg ttagtgtgac        50

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 39
atctcggtgt tggctggata gagccggtag gccctatcgt agggtgtgac        50

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 40

```
gtctcttttg tccgcgactc gaaatagtgt gttgaagcag ctctagtgac          50
```

<210> SEQ ID NO 41
<211> LENGTH: 54
<212> TYPE: DNA
<213> ORGANISM: Artificial Sequence
<220> FEATURE:
<223> OTHER INFORMATION: Description of Artificial Sequence:
     Synthetic Co-DNA

<400> SEQUENCE: 41

```
agccatagtt ctaccagcgg ttcgaaatag tgaagtgttc gtgactatcg gtaa    54
```

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence:
     Synthetic Co-DNA

<400> SEQUENCE: 42

```
ggtaagcttg gcac                                                14
```

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence:
     Synthetic Zn-DNA

<400> SEQUENCE: 43

```
ttttgtcagc gactcgaaat agtgtgttga agcagctcta                    40
```

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence:
     Synthetic Zn-DNA

<400> SEQUENCE: 44

```
ttttgtcagc gactcgaaat agtgtgttga agccgctcta                    40
```

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence:
     Synthetic Zn-DNA

<400> SEQUENCE: 45

```
ttttgtcagc gactcgaaat agtgtattgc agtagatcta                    40
```

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence:
     Synthetic Zn-DNA

<400> SEQUENCE: 46

```
ttttgtcagc gactcgaaat agtgtgttac agttgcccta                    40
```

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 47
ttttgtcagc gactcgaaat agagagtcga cacacctctc        40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 48
ttttgtcagc gactcgaaat agttagttga accagctctc        40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 49
ttttgtcagc gactcgaaat agtgagtaag aggagctatc        40

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 50
ttttgtcagc gactcgaaat agtgagggga aacagctctc        40

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 51
ttttgtcagc gactcgaaat agttagttga acacctctc        39

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic Zn-DNA

<400> SEQUENCE: 52
ttttgtcagc gactcgaaat attgagttga agcagatctc        40

```
<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 53
ttttgtcagc gacacgaaat agtgagttga ggcggcgctg          40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 54
tttttgcagc gacacgaaat agttagttga agaagctctt          40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 55
ttttgtcagc gactcgaaat agtcagttgt agcagctctt          40

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 56
ttttgtcagc gactcgaaat agtgcgtaga accagctctc          40

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 57
ttttgtcagc gacacgaaat agtgcggtgt atctgccctc          40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 58
ttttgtcagc gacacgaaat agtgtgatgt agtagctctc          40
```

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 59
ttttgtcagc gacacgaaat agtgtgacga atcatctc                           38

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 60
ttttgtcagc gacacgaaat agtgtgttta agcgctctc                          39

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 61
ttttgtcagc gacacgaaat agtgtgttga agcacgtctc                         40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 62
ttttgtcagc gactcgaaat agtttgttga agcagctctc                         40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 63
ttttgtcagc gactcgaaat agtgtattac agcagctctc                         40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 64
ttttgtcagc gactcgaaat agtgtgttga aacagctatc                         40

<210> SEQ ID NO 65

```
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 65
ttgtgcatgc tactcgtaat tgtgtctcga agcagctctc                                40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 66
gtcagtcagg tactcgaaaa atagtgttca agccgctgtc                                40

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 67
tttttgcagc gactcgaaag attgtgttga ggcggctatc                                40

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 68
ttctctcagc gactaaaaat agtgtgttga agcccctctc                                40

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 69
tattgtcagt gacccaaaat agtatgttga agcagctctg                                40

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence:
      Synthetic Zn-DNA

<400> SEQUENCE: 70
ttttgtcagc tactgaaata gtgttttgaa gaagtcctg                                 39

<210> SEQ ID NO 71
<211> LENGTH: 15
```

-continued

```
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
substra    te
<220> FEATURE:
<221> NAME/KEY: modified_base
<222> LOCATION: (8)
<223> OTHER INFORMATION: ribonucleotide base

<400> SEQUENCE: 71
tcactatagg aagag                                                      15

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate

<400> SEQUENCE: 72
ctcttcagcg atccggaacg gcacccatgt tagtga                               36

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate
<220> FEATURE:
<221> NAME/KEY: modified_base
<222> LOCATION: (8)
<223> OTHER INFORMATION: ribonucleotide base

<400> SEQUENCE: 73
tcactataag aagagatgg                                                  19

<210> SEQ ID NO 74
<211> LENGTH: 37
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate

<400> SEQUENCE: 74
acacatctct gaagtagcgc cgccgtatag tgacgct                              37

<210> SEQ ID NO 75
```

```
<211> LENGTH: 17
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate

<400> SEQUENCE: 75
ggagagagau gggugcg                                                    17

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate

<400> SEQUENCE: 76
cgcacccagg ctagctacaa cgactctctc c                                    31

<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate

<400> SEQUENCE: 77
aaguaacuag agaugga                                                    17

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate

<400> SEQUENCE: 78
cgcaccctcc gagccggacg aagttactt                                       29

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence:
      Synthetic chimeric
      substrate
```

```
<220> FEATURE:
<223> OTHER INFORMATION: Description of Combined DNA/RNA Molecule:
      Synthetic chimeric
      substrate
<220> FEATURE:
<221> NAME/KEY: modified_base
<222> LOCATION: (9)
OTHER INFORMATION: ribonucleotide ba    se

<400> SEQUENCE: 79
ctcactatag gaagagatg                                              19

<210> SEQ ID NO 80
<211> LENGTH: 41
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate

<400> SEQUENCE: 80
catctcttaa cggggctgtg cggctaggaa gtaatagtga g                     41

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate
<220> FEATURE:
<221> NAME/KEY: modified_base
<222> LOCATION: (10)
<223> OTHER INFORMATION: ribonucleotide base

<400> SEQUENCE: 81
actcactata ggaagagatg                                             20

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence:
      Synthetic chimeric
      substrate
<220> FEATURE:
<223> OTHER INFORMATION: Description of Combined DNA/RNA Molecule:
      Synthetic chimeric
      substrate

<400> SEQUENCE: 82
catctcttct ccgagccggt cgaaatagtg agt                              33

<210> SEQ ID NO 83
<211> LENGTH: 107
<212> TYPE: DNA
<213> ORGANISM: Artificial Sequence
<220> FEATURE:
<223> OTHER INFORMATION: Description of Combined DNA/RNA Molecule:
      Synthetic chimeric
```

```
        oligonucleotide
<220> FEATURE:
<223> OTHER INFORMATION: Description of Artificial Sequence: Predicted
      secondary structure of the G3 deoxyribozyme
<220> FEATURE:
<221> NAME/KEY: modified_base
<222> LOCATION: (28)
<223> OTHER INFORMATION: ribonucleotide base
<220> FEATURE:
<221> NAME/KEY: modified_base
<222> LOCATION: (67)
<223> OTHER INFORMATION: variable nucleotide
<220> FEATURE:
<221> NAME/KEY: modified_base
<222> LOCATION: (69)..(74)
<223> OTHER INFORMATION: variable nucleotide
<220> FEATURE:
<221> NAME/KEY: modified_base
<222> LOCATION: (80)..(82)
<223> OTHER INFORMATION: variable nucleotide
<220> FEATURE:
<221> NAME/KEY: modified_base
<222> LOCATION: (85)..(89)
<223> OTHER INFORMATION: variable nucleotide

<400> SEQUENCE: 83
gggacgaatt ctaatacgac tcactatagg aagagatggc gacaactctt tacccaagaa      60
ggggtgngnn nnnngctacn nnatnnnnnt gacggtagct tggcacc                   107

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence:
      Synthetic Co-DNA

<400> SEQUENCE: 84
cactatagga agagatggcg acatctcttg acccaagaag gggtg                      45

<210> SEQ ID NO 85
<211> LENGTH: 44
<212> TYPE: DNA
<213> ORGANISM: Artificial Sequence
<220> FEATURE:
<223> OTHER INFORMATION: Description of Combined DNA/RNA Molecule:
      Synthetic chimeric
      substrate
<220> FEATURE:
<223> OTHER INFORMATION: Description of Artificial Sequence: Synthetic
      chimeric oligonucleotide
<220> FEATURE:
<221> NAME/KEY: modified_base
<222> LOCATION: (22)
<223> OTHER INFORMATION: ribonucleotide base

<400> SEQUENCE: 85
tgtcaactcg tgactcacta taggaagaga tgtgtcaact cgtg                       44

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: see specification as filed for detailed
      description of
      preferred embodiments

<400> SEQUENCE: 86
```

-continued

```
cacgagttga ca                                                          12

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide 17E-C

<400> SEQUENCE: 87
catctcttcc ccgagccggt cgaaatagtg agt                                   33

<210> SEQ ID NO 88
<211> LENGTH: 12
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: see specification as filed for detailed
      description of
      preferred embodiments

<400> SEQUENCE: 88
cacgagttga ca                                                          12
```

NUCLEIC ACID ENZYME BIOSENSORS FOR IONS

CROSS REFERENCE TO RELATED APPLICATION

This is a divisional of U.S. application Ser. No. 09/605,558, filed on June 27, 2000, now U.S. Pat. No. 6,706,474, which is incorporated herein by reference to the extent permitted by law.

FEDERALLY SPONSORED RESEARCH OR DEVELOPMENT

The U.S. Government may have rights in the present invention pursuant to the terms of grant number R29 GM53706 awarded by the National Institutes of Health.

BACKGROUND

Many metals pose a risk as environmental contaminants. A well-known example is lead. Low level lead exposure can lead to a number of adverse health effects, with as many as 9–25% of pre-school children presently at risk. The level of lead in the blood considered toxic is $\geq 10$ µg/dL (480 nM). Current methods for lead analysis, such as atomic absorption spectrometry, inductively coupled plasma mass spectrometry, and anodic stripping voltammetry, often require sophisticated equipment, sample pre-treatment, and skilled operators.

Simple, rapid, inexpensive, selective and sensitive methods that permit real time detection of $Pb^{2+}$ and other metal ions are very important in the fields of environmental monitoring, clinical toxicology, wastewater treatment, and industrial process monitoring. Furthermore, methods are needed for monitoring free or bioavailable, instead of total, metal ions in industrial and biological systems.

Fluorescence spectroscopy is a technique well suited for very small concentrations of analytes. Fluorescence provides significant signal amplification, since a single fluorophore can absorb and emit many photons, leading to strong signals even at very low concentrations. In addition, the fluorescence time-scale is fast enough to allow real-time monitoring of concentration fluctuations. The fluorescent properties only respond to changes related to the fluorophore, and therefore can be highly selective. Furthermore, fluorometers for uses in the field are commercially available. Fluorescent detection is also compatible with fiber-optic technology and well suited for in vivo imaging applications. Several fluorescence-related parameters can be assessed for the purpose of sensing, including fluorescence intensity, emission or excitation wavelength, fluorescence lifetime and anisotropy.

Many fluorescent chemosensors, including fluorophore-labeled organic chelators (Rurack, et al., 2000; Hennrich et al., 1999; Winkler et al., 1998; Oehme & Wolfbeis, 1997) and peptides (Walkup & Imperiali, 1996; Deo & Godwin, 2000; Pearce et al., 1998), have been developed for metal ion detection. These ion sensors are usually composed of an ion-binding motif and a fluorophore. Metal detection using these fluorescent chemosensors relies on the modulation of the fluorescent properties of the fluorophore by the metal-binding event. Detection limits on the level of micromolar and even nanomolar concentrations have been achieved for heavy metal ions including $Zn^{2+}$, $Cu^{2+}$, $Hg^{2+}$, $Cd^{2+}$ and $Ag^{+}$. The design and synthesis of a chemosensor that exhibits highly selective and sensitive binding of the metal ion of choice in aqueous solution is still a big challenge, although the metal binding and the fluorescent moieties of the sensor can be systematically varied to achieve desired properties.

Nucleic acid molecules have previously been adapted to sense the presence of nucleic acids and to detect gene mutations from inherited diseases or chemical damages. In recent years, the molecular recognition and catalytic function of nucleic acids have been extensively explored. This exploration has lead to the development of aptamers and nucleic acid enzymes.

Aptamers are single-stranded oligonucleotides derived from an in vitro evolution protocol called systematic evolution of ligands by exponential enrichment (SELEX). Nucleic acid aptamers have been isolated from random sequence pools and can selectively bind to non-nucleic acid targets, such as small organic molecules or proteins, with affinities as high as $10^{-14}$ M (Uphoff et al., 1996; Famulok, 1999). Most aptamers undergo a conformational change when binding their cognate ligands. With this property, several DNA and RNA aptamers have been engineered to sense L-adenosine or thrombin through an internally labeled fluorescent reporter group (Jhaveri et al., 2000). Thus, the conformational change in the aptamer upon binding leads to a change in fluorescence.

Nucleic acid enzymes are nucleic acid molecules that catalyze a chemical reaction. In vitro selection of nucleic acid enzymes from a library of $10^{14}$–$10^{15}$ random nucleic acid sequences offers considerable opportunity for developing enzymes with desired characteristics (Breaker & Joyce, 1994; Breaker, 1997). Compared with combinatorial searches of chemo- and peptidyl-sensors, in vitro selection of DNA/RNA is capable of sampling a larger pool of sequences, amplifying the desired sequences by polymerase chain reactions (PCR), and introducing mutations to improve performance by mutagenic PCR.

Allosteric ribozymes (or aptazymes), which combine the features of both aptamer and catalytic RNA, also hold promises for sensing small molecules (Potyrailo et al., 1998; Koizumi et al., 1999; Robertson & Ellington, 1999, 2000). Their reactivity is modulated through the conformational changes caused by the binding of small organic molecules to an allosteric aptamer domain. Therefore, the signal of ligand binding can be transformed into a signal related to chemical reaction.

Divalent metal ions can be considered as a special class of cofactors controlling the activity of nucleic acid enzymes. The reaction rate of the nucleic acid enzymes depends on the type and concentration of the metal ion in solution. Several RNA and DNA enzymes obtained through in vitro selection are highly specific for $Cu^{2+}$, $Zn^{2+}$, and $Pb^{2+}$, with metal ion requirements on the level of micromolar concentrations (Breaker & Joyce, 1994; Pan & Uhlenbeck, 1992; Carmi et al., 1996; Pan et al., 1994; Cuenoud & Szotak, 1995; Li et al., 2000; Santoro et al., 2000).

BRIEF SUMMARY

The present invention uses nucleic acid enzymes as signal transducers for ion detection. Compared with fluorescent chemosensor and protein biosensors, nucleic acid-based sensors are more amenable to combinatorial search for sequences with desired metal specificity and affinity. In addition, DNA, in particular, is stable and can be readily synthesized. A wide range of fluorescent dyes can be easily introduced at specific sites to suit different needs. DNA-based biosensors can also be adapted for use with optical fiber and DNA-chip technology for applications such as in vivo imaging, in situ detection, and array sensing.

In one aspect, the present invention provides for specific and sensitive biosensors of ions. The biosensors are useful in methods of detecting the presence of an ion, particularly metal ions such as $Pb^{2+}$. In certain embodiments, the biosensors may be used to determine the concentration of a particular ion in a solution.

The biosensors of the present invention use nucleic acid enzymes that require the presence of specific ions for their activity. Enzymatic activity leads to hydrolytic cleavage of a substrate nucleic acid that may be part of the nucleic acid enzyme itself. The resulting cleavage product then may be detected indicating the presence of the ion.

In a preferred embodiment, the biosensor comprises a fluorophore and a quencher arranged in proximity such that prior to cleavage the fluorescence intensity is decreased by the quencher. However, upon cleavage, the fluorophore and quencher are separated leading to an increase in fluorescence intensity. In a further preferred embodiment, the biosensor contains an array of nucleic acid enzymes having a range of sensitivities and specificities to several different ions.

A "nucleic acid enzyme" is a nucleic acid molecule that catalyzes a chemical reaction. The nucleic acid enzyme may be covalently linked with one or more other molecules yet remain a nucleic acid enzyme. Examples of other molecules include dyes, quenchers, proteins, and solid supports. The nucleic acid enzyme may be entirely made up of ribonucleotides, deoxyribonucleotides, or a combination of ribo- and deoxyribonucleotides.

A "sample" may be any solution that may contain an ion (before or after pre-treatment). The sample may contain an unknown concentration of an ion. For example, the sample may be paint that is tested for lead content. The sample may be diluted yet still remain a sample. The sample may be obtained from the natural environment, such as a lake, pond, or ocean, an industrial environment, such as a pool or waste stream, a research lab, common household, or a biological environment, such as blood. Of course, sample is not limited to the taking of an aliquot of solution but also includes the solution itself. For example, a biosensor may be placed into a body of water to measure for contaminants. In such instance, the sample may comprise the body of water or a particular area of the body of water. Alternatively, a solution may be flowed over the biosensor without an aliquot being taken. Furthermore, the sample may contain a solid or be produced by dissolving a solid to produce a solution. For example, the solution may contain soil from weapon sites or chemical plants.

"Measuring the product of the nucleic acid enzymatic reaction" includes measuring the result of the production of a product by an enzyme. For example, in an embodiment where the substrate comprises a quencher and the enzyme comprises a fluorophore and cleavage of the substrate by the enzyme leads to dissociation of the product from the enzyme, "measuring the product" includes detecting the increase of fluorescence. Thus, one is measuring the product by detecting its inability to quench fluorescence.

"Contacting a nucleic acid enzyme with a sample" includes placing the sample and enzyme in proximity such that an ion in the sample could be used as a cofactor. "Contacting" includes such acts as pipetting a sample onto a solid support or into a tube or well containing the nucleic acid enzyme. Alternatively, the enzyme may be brought to the sample. For example, the enzyme may be placed into a stream to monitor for the presence of a contaminant.

BRIEF DESCRIPTION OF THE DRAWINGS

FIG. 1. Selection scheme for RNA-cleaving deoxyribozymes.

FIG. 2. (SEQ ID NOS 13–23, respectively, in oredr of appearance) Sequence classes of the clones Zn-DNA. The numbers on the left are the clone-numbers randomly assigned to the sequence during the cloning and sequencing process. The highly conserved sequences (Region-20nt) are in bold. The covariant nucleotides are underlined. The 5'- and the 3"-primer binding sequences are shown in italic.

FIG. 3. (SEQ ID NOS 24–42, respectively, in order of appearance) Sequence classes of the cloned Co-DNA. The clone-numbers are listed on the left. The 540 and the 341 primer binding sequences are in italic.

FIG. 7. Comparison of G3 deoxyribozyme with class II Co-DNA.

FIG. 8. Steady-state fluorescence spectra of the substrate (Rh-17DS) alone (I), after annealing to the deoxyribozyme (17E-Dy) (II), and 15 min after adding 500 nM Pb(OAc)$_2$ (III).

FIG. 9. The fluorescence response rate (vfluo) of Rh-17EDS-Dy for different divalent metal ions. The "control" was measured without Pb(II) or transition metal ions.

FIG. 10. Dependence of $v_{fluo}$ on the concentration of $Pb^{2+}$ or $CO^{2+}$. The reaction was carried out in the presence of 50 mM NaCl in 50 mM HEPES (pH 7.5).

FIG. 11. DNA chips for ion sensing.

DETAILED DESCRIPTION

Figure 1A:
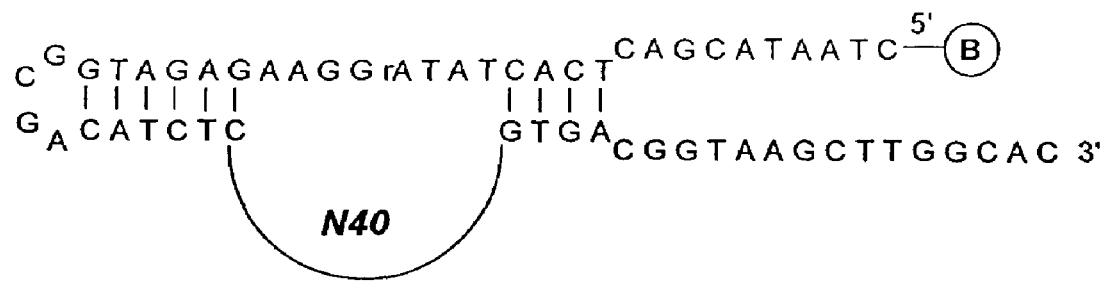
FIG. 1A. (SEQ ID NO: 12) Starting pool of random-sequenced DNAs, engineered to contain two substrate-binding domains. Each member of the pool contains a 5' terminal biotin (encircled B), a single embedded ribonucleotide (rA) and a 40-nucleotide random sequence domain (N40).

The invention described herein represents a new class of ion sensors and is the first example of a DNA enzyme-based biosensor for ions. It combines the high selectivity of DNA enzymes with the high sensitivity of fluorescence detection. For example, in one embodiment, selectivity for $Pb^{2+}$ was >80 fold over other divalent metal ions with high sensitivity (>400% signal increase). Such selectivity and sensitivity provides for qualitative and quantitative detection of ions over a concentration range of several orders of magnitude. In a preferred embodiment, the fluorescence domain is decoupled from the ion-recognition/catalysis domain, and therefore the sensitivity and selectivity of this system may be manipulated by a careful choice of fluorophores and by performing in vitro selection of ion-binding domains to not only keep sequences reactive with the ion of choice, but also remove sequences that also respond to other ions.

In addition, DNA is stable, inexpensive and easily adaptable to optical fiber and chip technology for device manufacture. The attachment of DNA enzymes to optical fibers or chips allows regeneration of the sensors by washing away the cleavage products and adding new substrates. Finally, sequences specific for other ions and with various detection ranges may be isolated by varying the selection conditions, providing for a highly sensitive and selective fluorosensor system.

Nucleic Acid Enzymes

A growing number of nucleic acid enzymes have been discovered or developed showing a great diversity in catalytic activity (Table 1 and Table 2). Many if not all of the enzymes are dependent on one or more ion cofactors. In vitro selection may be used to "enhance" selectivity and sensitivity for a particular ion. Such enzymes find particular utility in the compositions and methods of the present invention. For example, nucleic acid enzymes that catalyze molecular association (ligation, phophorylation, and amide bond formation) or dissociation (cleavage or transfer) are particularly useful.

In preferred embodiments, a nucleic acid enzyme that catalyzes the cleavage of a nucleic acid in the presence of an ion is used. The nucleic acid enzyme may be RNA (ribozyme), DNA (deoxyribozyme), a DNA/RNA hybrid enzyme, or a peptide nucleic acid (PNA) enzyme. PNAs comprise a polyamide backbone and the bases found in naturally occurring nucleosides and are commercially available from, e.g., Biosearch, Inc. (Bedford, Mass.).

Ribozymes that may be used in the present invention include, but are not limited to, group I and group II introns, the RNA component of the bacterial ribonuclease P, hammerhead, hairpin, hepatitis delta virus and Neurospora VS ribozymes. Also included are in vitro selected ribozymes, such as those isolated by Tang and Breaker (2000).

One limitation of using a ribozyme is that they tend to be less stable than deoxyribozymes. Thus, in preferred embodiments, the nucleic acid enzyme is a deoxyribozyme. Preferred deoxyribozymes include those shown in FIG. 6A-6F and deoxyribozymes with extended chemical functionality (Santoro et al., 2000).

TABLE 1

Reactions catalyzed by ribozymes that were isolated from in vitro selection experiments.

| Reaction | $k_{cat}$ (min$^{-1}$) | $k_m$ (μM) | $k_{cat}/k_{uncat}$[a] | Reference |
|---|---|---|---|---|
| Phosphoester centers | | | | |
| Cleavage | 0.1 | 0.03 | $10^5$ | Vaish, 1998 |
| Transfer | 0.3 | 0.02 | $10^{13}$ | Tsang, 1996 |
| Ligation | 100 | 9 | $10^9$ | Ekland, 1995 |
| Phosphorylation | 0.3 | 40 | >$10^5$ | Lorsch, 1994 |
| Mononucleotide polymerization | 0.3 | 5000 | >$10^7$ | Ekland, 1996 |
| Carbon centers | | | | |
| Aminoacylation | 1 | 9000 | $10^6$ | Illangasekare, 1997 |
| Aminoacyl ester hydrolysis | 0.02 | 0.5 | 10 | Piccirilli, 1992 |
| Aminoacyl transfer | 0.2 | 0.05 | $10^3$ | Lohse, 1996 |
| N-alkylation | 0.6 | 1000 | $10^7$ | Wilson, 1995 |
| S-alkylation | $4 \times 10^{-3}$ | 370 | $10^3$ | Wecker, 1996 |
| Amide bond cleavage | $1 \times 10^{-5}$ | | $10^2$ | Dai, 1995 |
| Amide bond formation | 0.04 | 2 | $10^5$ | Wiegand, 1997 |
| Peptide bond formation | 0.05 | 200 | $10^6$ | Zhang, 1997 |
| Diels-Alder cycloaddition | >0.1 | >500 | $10^3$ | Tarasow, 1997 |
| Others | | | | |
| Biphenyl isomerization | $3 \times 10^{-5}$ | 500 | $10^2$ | Prudent, 1994 |
| Porphyrin metallation | 0.9 | 10 | $10^3$ | Conn, 1996 |

[a]Reactions catalyzed by ribozymes that were isolated from in vitro selection experiments. kcat/kuncat is the rate enhancement over uncatalyzed reaction.

TABLE 2

Deoxyribozymes isolated through in vitro selection.

| Reaction | Cofactor | $k_{max}$(min$^{-1}$)[a] | $k_{cat}/k_{uncat}$ | Reference |
|---|---|---|---|---|
| RNA transesterification | $Pb^{2+}$ | 1 | $10^5$ | Breaker, 1994 |
| | $Mg^{2+}$ | 0.01 | $10^5$ | Breaker, 1995 |
| | $Ca^{2+}$ | 0.08 | $10^5$ | Faulhammer, 1997 |
| | $Mg^{2+}$ | 10 | >$10^5$ | Santoro, 1997 |
| | None | 0.01 | $10^8$ | Geyer, 1997 |
| | L-histidine | 0.2 | $10^6$ | Roth, 1998 |
| | $Zn^{2+}$ | ~40 | >$10^5$ | Li, J., 2000 |
| DNA cleavage | $Cu^{2+}$ | 0.2 | >$10^6$ | Carmi, 1996 |
| DNA ligation | $Cu^{2+}$ or $Zn^{2+}$ | 0.07 | $10^5$ | Cuenod, 1995 |
| DNA phosphorylation | $Ca^{2+}$ | 0.01 | $10^9$ | Li, Y., 1999 |

TABLE 2-continued

Deoxyribozymes isolated through in vitro selection.

| Reaction | Cofactor | $k_{max}(min^{-1})^a$ | $k_{cat}/k_{uncat}$ | Reference |
|---|---|---|---|---|
| 5',5'-pyrophophate formation | $Cu^{2+}$ | $5 \times 10^{-3}$ | $>10^{10}$ | Li, Y., 2000 |
| Porphyrin metalation | None | 1.3 | $10^3$ | Li, Y., 1996 |

$^a k_{max}$ is the maximal rate constant obtained under optimized conditions.

An advantage of ribozymes and deoxyribozymes is that they may be produced and reproduced using biological enzymes and appropriate templates. However, the present invention is not limited to ribozymes and deoxyribozymes. Nucleic acid enzymes that are produced by chemical oligo-synthesis methods are also included. Thus, nucleic acids including nucleotides containing modified bases, phosphate, or sugars may be used in the compositions and methods of the present invention. Modified bases are well known in the art and include inosine, nebularine, 2-aminopurine riboside, $N^7$-denzaadenosine, and $O^6$-methylguanosine (Earnshaw & Gait, 1998). Modified sugars and phosphates are also well known and include 2'-deoxynucleoside, abasic, propyl, phosphorothioate, and 2'-O-allyl nucleoside (Earnshaw & Gait, 1998). DNA/RNA hybrids and PNAs may be used in the compositions and methods of the present invention. The stability of PNAs and relative resistance to cellular nucleases make PNA enzymes amenable to in vivo applications.

In certain embodiments, the substrate for the nucleic acid enzyme and the enzyme itself are contained in the same nucleic acid strand. Such enzymes are cis-acting enzymes. Examples include the $Zn^{2+}$-dependent deoxyribozymes (Zn-DNA) created in Example 1 (FIG. 1A and FIG. 2).

Figure 5:
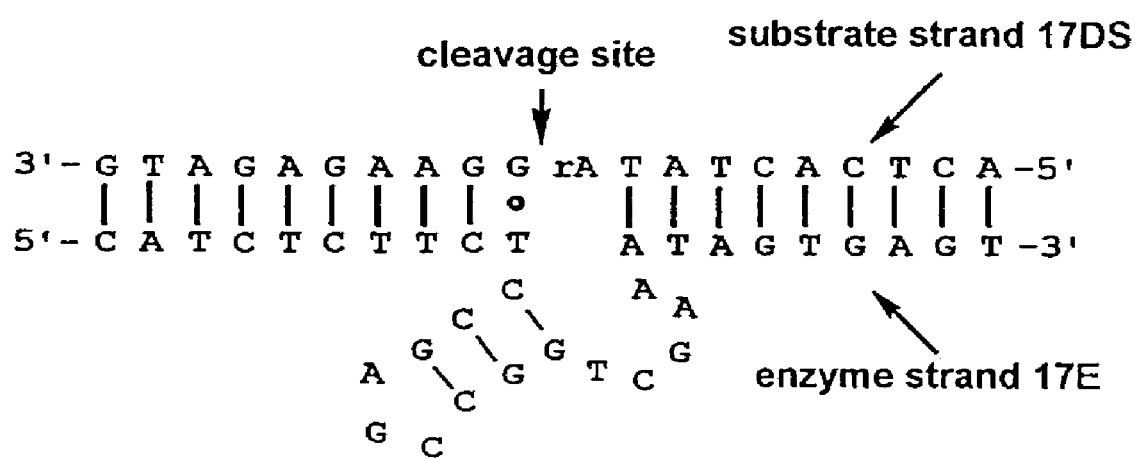
FIG. 5. (SEQ ID NOS 1–2) Proposed secondary structure of the Zn(II)-dependent trans-cleaving deoxyribozyme.

In preferred embodiments, the nucleic acid enzyme cleaves a nucleic acid strand that is separate from the strand comprising the enzyme (trans-acting). One advantage of utilizing trans-activity is that, after cleavage, the product is removed and additional substrate may be cleaved by the enzymatic strand. A preferred nucleic acid enzyme is 5'-CATCTCTTCTCCGAGCCGGTCGAAATAGTGAGT-3' (17E; FIG. 5; SEQ ID NO:1). The corresponding preferred substrate to 17E is 5'-ACTCACTATrAGGAAGAGATG-3' (17DS; FIG. 5; SEQ ID NO:2), where rA denotes a single ribonucleotide.

It may be beneficial to use directed mutation to change one or more properties of a nucleic acid enzyme or its substrate. Using 17E and 17DS as an example, one may wish to alter the avidity of the two arms of the hybridized enzyme and substrate. The "arms" are those areas displaying Watson-Crick basepairing in FIG. 5. To alter avidity, one may increase or decrease the length of the arms. Increasing the length of the arms increases the number of Watson-Crick bonds, thus increasing the avidity. The opposite is true for decreasing the length of the arms. Decreasing the avidity of the arms facilitates the removal of substrate from the enzyme, thus allowing faster enzymatic turnover.

Another method of decreasing avidity includes creating mismatches between the enzyme and the substrate. Alternatively, the G-C content of the arms may be altered. Of course, the effect of any directed change should be monitored to ensure that the enzyme retains its desired activity, including ion sensitivity and selectivity. In light of the present disclosure, one of skill in the art would understand how to monitor for a desired enzymatic activity. For example, to ensure that the mutated enzyme maintained sensitivity and selectivity for $Pb^{2+}$, one would test to determine if the mutated enzyme remained reactive in the presence of lead (sensitivity) and maintained its lower level of activity in the presence of other ions (selectivity).

In preferred embodiments, the nucleic acid enzyme is sensitive and selective for a single ion. The ion may be any anion or cation. The ion may be monovalent, divalent, trivalent, or polyvalent. Examples of monovalent cations include $K^+$, $Na^+$, $Li^+$, $Tl^+$, $NH_4^+$, and $Ag^+$. Examples of divalent cations include $Mg^{2+}$, $Ca^{2+}$, $Mn^{2+}$, $Co^{2+}$, $Ni^{2+}$, $Zn^{2+}$, $Cd^{2+}$, $Cu^{2+}$, $Pb^{2+}$, $Hg^{2+}$, $Pt^{2+}$, $Ra^{2+}$, $Ba^{2+}$, and $Sr^{2+}$. Examples of trivalent cations include $Co^{3+}$, $Cr^{3+}$, and lanthanide ions ($Ln^{3+}$). Polyvalent cations include $Ce^{4+}$, spermine, and spermidine. Because, in certain embodiments, the biosensors of the present invention are used to monitor contaminants in the environment, preferred ions are those that are toxic to living organisms, e.g., $Ag^+$, $Pb^{2+}$ and $Hg^{2+}$.

Often the nucleic acid enzymes that have activity with one ion also have at least some activity with one or more other ions. Such multi-sensitive enzymes may still be used in the compositions and methods of the present invention. However, it should be understood that use of a multi-sensitive enzyme may lead to uncertainty as to which of the ions is present. In such cases, measuring the rate of enzymatic activity, using serial dilutions, or using an array of nucleic acid enzymes may be helpful in deciphering which ion is present.

In Vitro Selection of Nucleic Acid Enzymes

Many nucleic acid enzymes that are dependent on ions, particularly metal ions, for activity are known in the art (Breaker & Joyce, 1994; Pan & Uhlenbeck, 1992; Cuenoud & Szostak, 1995; Carmi et al., 1996; Li et al., 2000; Santoro et al., 2000). In light of the present disclosure, one of skill in the art would understand how to utilize a known nucleic acid enzyme in the methods and biosensors of the present invention. Furthermore, the present invention may include a nucleic acid enzyme created by in vitro selection. Methods of in vitro selection of nucleic acid enzymes are known in the art and described herein.

In vitro selection is a technique in which RNA or DNA molecules with certain functions are isolated from a large number of sequence variants through multiple cycles of selection and amplification (Joyce, 1994; Chapman et al., 1994). The concept of in vitro selection of catalytic RNA molecules was first introduced in the late 1980's. Since then, it has been widely applied to obtain ribozymes with maximized activities or novel catalytic abilities, and to identify oligonucleotides (called aptamers) that bind to certain proteins or small molecules with high affinity. The process for aptamers selection is sometimes referred as systematic evolution of ligands by exponential enrichment (SELEX)(Tuerk & Gold, 1990).

The first catalytic DNA (deoxyribozyme) was isolated by Breaker and Joyce in 1994 through in vitro selection. This deoxyribozyme is able to catalyze phosphodiester cleavage reaction in the presence of $Pb^{2+}$. Unlike RNA-based catalysts, DNA molecules with catalytic functions have not been encountered in nature, where DNA exists primarily as base-paired duplex and serves mainly as the carrier of genetic information. The identification of DNA molecules with catalytic functions further demonstrated the power of in vitro selection.

In vitro selection is typically initiated with a large collection of randomized sequences. A typical DNA or RNA library for selection contains $10^{13}$–$10^{16}$ sequence variants.

The construction of a completely randomized pool is accomplished by chemical synthesis of a set of degenerated oligonucleotides using standard phosphoramidite chemistry. The 3'-phosphoramidite compounds of four nucleosides (A, C, G, and T) are premixed before being supplied to an automated DNA synthesizer to produce oligonucleotides. By controlling the ratio of four phosphoroamidites, the identity at each nucleotide position can be either completely random, i.e. with equal chance for each base, or biased toward a single base. Other strategies for creating a randomized DNA library include applying mutagenic polymerase chain reaction (PCR) and template-directed mutagenesis (Tsang and Joyce, 1996; Cadwell and Joyce, 1992, 1994). For the purpose of in vitro selection of functional RNA molecules, the randomized DNA library is converted to an RNA library through in vitro transcription.

In vitro selection takes advantage of a unique property of RNA and DNA, i.e., the same molecule can possess both genotype (coding information) and phenotype (encoded function). The DNA or RNA molecules in the randomized library are screened simultaneously. Those sequences that exhibit a desired function (phenotype) are separated from the inactive molecules. Usually the separation is performed through affinity column chromatography, being linked to or released from a solid support, gel electrophoresis separation, or selective amplification of a tagged reaction intermediate. The genotype of the active molecules are then copied and amplified, normally through polymerase chain reaction (PCR) for DNA or isothermal amplification reaction for RNA (Guatelli et al., 1990). Mutations can be performed with mutagenic PCR to reintroduce diversity to the evolving system. These three steps—selection, amplification and mutation, are repeated, often with increasing selection stringency, until sequences with the desired activity dominate the pool.

Novel nucleic acid enzymes isolated from random sequences in vitro have extended the catalytic repertoire of RNA and DNA far beyond what has been found in nature. The selected ribozymes are capable of catalyzing a wide range of reactions at both phosphate and non-phosphate centers (Table 1). The reactions that are catalyzed by deoxyribozymes are less diverse, compared with the ribozymes (Table 2). However, the catalytic rate ($k_{cat}$) of most deoxyribozymes is comparable to that of the ribozymes catalyzing the same reaction. In certain cases, the catalytic efficiency ($k_{cat}/K_m$) of nucleic acid enzymes even exceeds that of the protein enzymes.

Figure 6A:
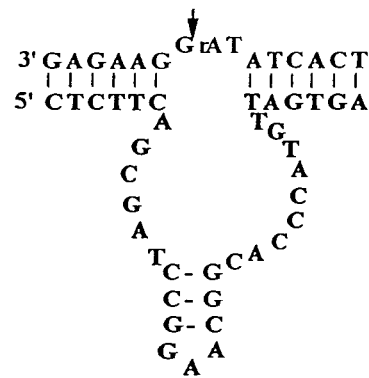
FIG. 6A. (SEQ ID NOS 71& 72) and FIG. 6B. (SEQ ID NOS 73& 74) THE deoxyribozyme selected using $Mg^{2+}$or $Pb^{2+}$as cofactor (Breaker & Joyce, 1994, 1995).
Figure 6B:
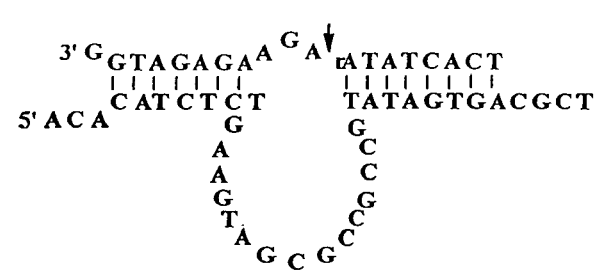
FIG. 6. Sequences and proposed secondary-structures of several RNA-cleaving deoxyribozymes.
FIG. 6C.
FIG. 6D. The 10–23 and the 8–17 deoxyribozymes selected in $Mg^{2+}$to cleave all-RNA substrate (Santoro & Joyce, 1997).
FIG. 6E. A deoxyribozyme selected using L-histidine as cofactor.
FIG. 6F. The 17E deoxyribozyme selected in $Zn^{2+}$. In each structure, the upper strand is the substrate and the lower strand is the enzyme. Arrows identify the site of RNA transesterification.
Figure 6C:
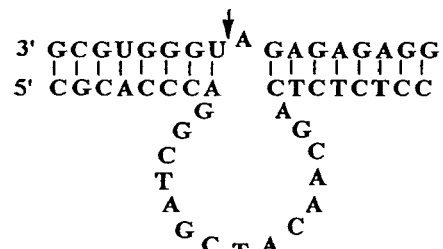
Figure 6D:
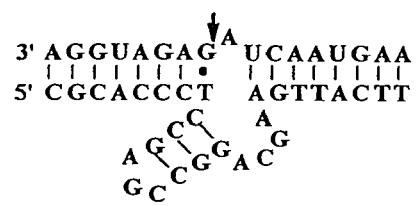
Figure 6E:
Figure 6F:
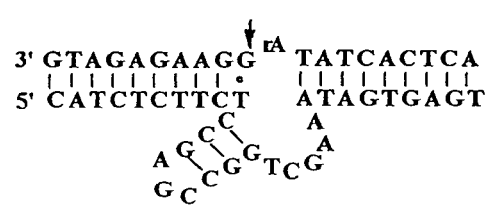

In vitro selection can be used to change the ion specificity or binding affinity of existing ribozymes, or to obtain nucleic acid enzymes specific for desired ions. For example, in vitro-selected variants of the group I intron (Lehman & Joyce, 1993) and the RNase P ribozyme (Frank & Pace, 1997) have greatly improved activity in $Ca^{2+}$, which is not an active metal ion cofactor for native ribozymes. The $Mg^{2+}$ concentration required for optimal hammerhead ribozyme activity has been lowered using in vitro selection to improve the enzyme performance under physiological conditions (Conaty et al., 1999; Zillman et al., 1997). Breaker and Joyce have isolated several RNA-cleaving deoxyribozymes using $Mg^{2+}$, $Mn^{2+}$, $Zn^{2+}$, or $Pb^{2+}$ as the cofactor (Breaker & Joyce, 1994, 1995). Only the sequence and structure of the $Pb^{2+}$-dependent and the $Mg^{2+}$-dependent deoxyribozymes were reported (FIGS. 6A and 6B). Other examples of metal-specific RNA/DNA enzymes obtained through in vitro selection include a $Pb^{2+}$-specific RNA-cleaving ribozyme (called leadzyme) (Pan & Uhlenbeck, 1992), a $Cu^{2+}$-specific DNA-cleaving deoxyribozyme (Carmi et al., 1996), and a DNA ligase active in $Zn^{2+}$ and $Cu^{2+}$ (Cuonod & Szostak, 1995).

Often nucleic acid enzymes developed for a specific metal ion by in vitro selection will have activity in the presence of other metal ions. For example, 17E deoxyribozyme was developed by in vitro selection for activity in the presence of $Zn^{2+}$. Surprisingly, the enzyme showed greater activity in the presence of $Pb^{2+}$ than $Zn^{2+}$. Thus, although produced in a process looking for $Zn^{2+}$-related activity, 17E may be used as a sensitive and selective sensor of $Pb^{2+}$.

To produce nucleic acid enzymes with greater selectivity, a negative selection step may be included in the process. For Example, $Pb^{2+}$-specific deoxyribozymes may be isolated using a similar selection scheme as for the selection of $Co^{2+}$- and $Zn^{2+}$-dependent DNA enzymes described in Example 1. In order to obtain deoxyribozymes with high specificity for $Pb^{2+}$, negative-selections may be carried out in addition to the positive selections in the presence of $Pb^{2+}$.

For negative selection, the DNA pool is selected against a "metal soup", which contains various divalent metal ions (e.g. $Mg^{2+}$, $Ca^{2+}$, $Mn^{2+}$, $Zn^{2+}$, $Cd^{2+}$, $Co^{2+}$, $Cu^{2+}$, etc.). Those sequences that undergo self-cleavage in the presence of divalent metal ions other than $Pb^{2+}$ are then washed off the column. The remaining sequences are further selected with $Pb^{2+}$ as the cofactor. $Pb^{2+}$-dependent deoxyribozymes with different affinities for $Pb^{2+}$ can be obtained by controlling the reaction stringency ($Pb^{2+}$ concentration).

Fluorophores and Quenchers

Any chemical reaction that leads to a fluorescent or chemiluminescent signal may be used in the compositions and methods of the present invention. In preferred embodiments, fluorophores are used to measure enzymatic activity and, thus, detect the presence of a particular ion. Essentially any fluorophore may be used, including BODIPY, fluoroscein, fluoroscein substitutes (Alexa Fluor dye, Oregon green dye), long wavelength dyes, and UV-excited fluorophores. These and additional fluorphores are listed in *Fluorescent and Luminescent Probes for Biological Activity. A Practical Guide to Technology for Quantitative Real-Time Analysis*, Second Ed. W. T. Mason, ed. Academic Press (1999) (incorporated herein by reference). In preferred embodiments, the fluorophore is 6-carboxytetramethylrhodamin (TAMRA). TAMRA has an excitation range of 500–550 nm and an emission range of 560–650 nm.

In certain embodiments, the substrate is labeled with a fluorophore and measurement of enzymatic activity is done by detecting the non-hybridized cleavage products in solution. Preferably, this is done by measuring the level of fluorescence in solution without detecting fluorescence from the bound substrate. This may be done by creating a flow such that, once the cleavage product enters the solution, it is carried away by the flow. Fluorescence of the flow is then measured in an area away from the enzyme-substrate pairs.

In preferred embodiments, the substrate is labeled with a fluorophore but fluorescence is quenched by a nearby quenching molecule. Quenching molecules absorb the energy of the excited fluorophore. Close proximity of fluorophore and quencher allow for the energy to be transferred from the fluorophore to the quencher. By absorbing this energy, the quencher prevents the fluorophore from releasing the energy in the form of a photon.

Quenchers may be categorized as non-fluorescent and fluorescent quenchers. Non-fluorescent quenchers are capable of quenching the fluorescence of a wide variety of fluorophores. Generally, non-fluorescent quenchers absorb energy from the fluorophore and release the energy as heat. Examples of non-fluorescent quenchers include DABCYL, QSY-7, and QSY-33.

Fluorescent quenchers tend to be specific to fluorophores that emit at a specific wavelength range. Fluorescent quenchers often involve fluorescence resonance energy transfer (FRET). In many instances the second molecule is also a fluorophore. In such cases, close proximity of the fluorophore and quencher is indicated by a decrease in fluorescence of the "fluorophore" and an increase in fluorescence in the fluorescent quencher. Commonly used fluorescent fluorophore pairs (fluorophore/fluorescent quencher) include fluorescein/tetramethylrhodamine, IAEDANS/fluorescein, fluorescein/fluorescein, and BODIPY FL/BODIPY FL.

The quencher may be located on a support such that it is in proximity with the fluorophore when the substrate is bound to the enzyme. In preferred embodiments, the quencher is linked to the enzyme. Even more preferred is to have the fluorphore linked to the 5' end of the substrate and the quencher linked to the 3' end of the enzyme such that when the substrate and enzyme are hybridized, the fluorophore and the quencher are in close proximity to each other. Upon cleavage of the substrate, the product disassociates from the enzyme. Dissociation removes the fluorophore from the quencher, leading to an increase in fluorescence (FIG. 8).

Of course, it would be understood that the fluorophore could be linked essentially anywhere on the substrate and quencher essentially anywhere on the enzyme, as long as they are in close proximity to each other when the enzyme is hybridized to the substrate. By close proximity, it is meant that they are situated such that the quencher is able to function. Furthermore, the quencher may be placed on the substrate and the fluorophore on the enzyme. Alternatively, both quencher and fluorophore may be linked to the substrate on opposite ends from the potential cleavage site. Cleavage of such a molecule would lead to dissociation of the two ends and thus separation of the fluorophore and quencher, leading to an increase in fluorescence. Similarly, in embodiments wherein the enzyme and the substrate are contained within the same nucleic acid strand, the fluorophore and quencher may be placed on opposite ends of the cleavage site.

When choosing a fluorophore, quencher, or where to position the molecules, it is important to consider, and preferably to test, the effect of the fluorphore or quencher on the enzymatic activity of the nucleic acid enzyme. Also, it is preferable that the fluorophore display a high quantum yield and energy transfer efficiency. Long-wavelength (excitation and emission) fluorophores are preferred because of less interference from other absorbing species. The fluorophore should also be less sensitive to pH change or to non-specific quenching by metal ions or other species.

Methods and devices for detecting fluorescence are well developed. Essentially any instrument or method for detecting fluorescent emissions may be used. For example, WO 99/27351 (incorporated herein in its entirety) describes a monolithic bioelectronical device comprising a bioreporter and an optical application specific integrated circuit (OA-SIC). The device allows remote sampling for the presence of substances in solution.

Furthermore, the fluorescence may be measured by a number of different modes. Examples include fluorescence intensity, lifetime, and anisotropy in either steady state or kinetic rate change modes (Lakowicz, 1999).

Sometimes other factors in a solution such as pH, salt concentration or ionic strength, or viscosity will have an effect on fluorescence. Others may affect the hybridization of the substrate and enzyme. Therefore, in preferred methods, controls are run to determine if the solution itself, regardless of enzymatic activity, is altering the fluorescence. Such controls include the use of non-cleavable substrates and or substrate without the presence of enzyme.

Biosensors

Described herein are nucleic acid enzymes that are dependent on the presence of a specific ion for activity. Using fluorophores or fluorophore/quencher labeling, it is possible to measure enzymatic activity, even in real time. These qualities make the compositions of the present invention excellent for use in biosensors for detecting ions.

Many biosensors utilizing nucleic acids are known in the art. For example, biosensors using aptamers have been developed for detecting molecules such as thrombin or adenosine (Potyrailo et al., 1999; Lee & Walt, 2000). In light of the present disclosure, one of ordinary skill in the art would know how to modify the nucleic acid biosensors to include nucleic acid enzymes.

In a simple embodiment, a biosensor of the present invention comprises a nucleic acid enzyme labeled with a quencher, a substrate labeled with a fluorophore, and a device to detect fluorescence such as a fluorescence microscope or a fluorometer. In a method using this embodiment, the enzyme and substrate are contacted with a sample suspected of containing an ion to which the enzyme is sensitive. Fluorescence is measured and compared to a control wherein the ion is absent. Change in fluorescence is indicative of the presence of the ion.

Of course, many variants of even this simple embodiment are included within the scope of the invention. Such variants include placing the enzyme, substrate, and sample in the well of a microtiter plate and measuring fluorescence with a microtiter plate reader. In another variation, the enzyme is attached to a solid support. When the enzyme is attached to a solid support, it is preferable that a linker is used. An exemplary linking system is biotin/streptavidin. For example, the biotin molecule may be linked to the enzyme and a plate may be coated with streptavidin. When linking an enzyme to a solid support, it is important to determine the effect of linkage on the enzymatic activity of the enzyme.

In an alternative embodiment, the solid support may be a bead and fluorescence measured using a flow cytometer. In embodiments having the enzyme attached to a solid support, the biosensor may be reusable. Old substrate and sample is removed, leaving the enzyme in place. New substrate and sample may then be added.

In another embodiment, the nucleic acid enzyme may be used in conjunction with fiber-optics (Lee & Walt, 2000). The nucleic acid enzyme may be immobilized on the surface of silica microspheres and distributed in microwells on the distal tip of an imaging fiber. The imaging fiber may then be coupled to a epifluorescence microscope system.

In certain embodiments, the biosensor will comprise an array of nucleic acid enzymes. The arrays of the present invention provide for the simultaneous screening of a variety of ion by nucleic acid enzymes. The array may contain as little as 2 or as many as 10,000 different nucleic acid enzymes. Of course, any integer in between may be used. Preferably, each individual nucleic acid enzyme has a measurable difference in specificity or affinity for at least one ion compared to at least one other nucleic acid enzyme within the array.

In preferred embodiments, the array is a high-density array like those used in DNA-chip technologies. Methods of forming high density arrays of nucleic acids with a minimal number of synthetic steps are known. (U.S. Pat. No. 6,040,138). The nucleic acid array can be synthesized on a solid support by a variety of methods, including light-directed chemical coupling, and mechanically directed coupling (U.S. Pat. No. 5,143,854; WO 90/15070; WO 92/10092; WO 93/09668). Using this approach, one heterogenous array of polymers is converted, through simultaneous coupling at a number of reaction sites, into a different heterogenous array.

The light-directed combinatorial synthesis of nucleic acid arrays on a glass surface uses automated phosphoramidite chemistry and chip masking techniques. In one specific implementation, a glass surface is derivatizied with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different nucleic acid analogues at different locations on the array is determined by the pattern of illumination during synthesis and the order of addition of coupling reagents.

In the event that a PNA is used in the procedure, it is generally inappropriate to use phosphoramidite chemistry to perform the synthetic steps, since the monomers do not attach to one another via a phosphate linkage. Instead, peptide synthetic methods are substituted (U.S. Pat. No. 5,143,854).

In addition to the foregoing, additional methods which can be used to generate an array of nucleic acids on a single solid support are known (For example, WO 93/09668). In these methods, reagents are delivered to the solid support by either (1) flowing within a channel defined on predefined regions or (2) "spotting" on predefined regions. However, other approaches, as well as combinations of spotting and flowing, may be employed. In each instance, certain activated regions of the solid support are mechanically separated from other regions when the monomer solutions are delivered to the various reaction sites.

A typical "flow channel" method applied to the nucleic acid enzyme arrays of the present invention can generally be described as follows. Diverse nucleic acid sequences are synthesized at selected regions of a solid support by forming flow channels on a surface of the solid support through which appropriate reagents flow or in which appropriate reagents are placed. For example, assume a monomer "A" is to be bound to the solid support in a first group of selected regions. If necessary, all or part of the surface of the solid support in all or a part of the selected regions is activated for binding by, for example, flowing appropriate reagents through all or some of the channels, or by washing the entire solid support with appropriate reagents. After placement of a channel block on the surface of the solid support, a reagent having the monomer A flows through or is placed in all or some of the channel(s). The channels provide fluid contact to the first selected regions, thereby binding the monomer A on the solid support directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the solid support; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the solid support at this stage of processing will be, for example, A, B, and AB. The process is repeated to form a vast array of nucleic acid enzymes of desired length and sequence at known locations on the solid support.

After the solid support is activated, monomer A can be flowed through some of the channels, monomer B can be flowed through other channels, a monomer C can be flowed through still other channels, etc. In this manner, many or all of the reaction regions are reacted with a monomer before the channel block must be moved or the solid support must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the solid support. For example, according to some embodiments, a protective coating such as a hydrophilic or hydrophobic coating (depending upon the nature of the solvent) is utilized over portions of the solid support to be protected, sometimes in combination with materials that facilitate wetting by the reactant solution in other regions. In this manner, the flowing solutions are further prevented from passing outside of their designated flow paths.

The "spotting" methods of preparing nucleic acid arrays can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire solid support surface can be sprayed or otherwise coated with a solution. In preferred embodiments, a dispenser moves from region to region, depositing only as much monomer as necessary at each stop. Typical dispensers include a micropipette to deliver the monomer solution to the solid support and a robotic system to control the position of the micropipette with respect to the solid support. In other embodiments, the dispenser includes a series of tubes, a manifold, an array of pipettes, or the like so that various reagents can be delivered to the reaction regions simultaneously.

Methods of detecting fluorescent signals on a DNA chip are well known to those of skill in the art. In a preferred embodiment, the nucleic acid enzyme array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

A confocal microscope may be automated with a computer-controlled stage to automatically scan the entire high density array. Similarly, the microscope may be equipped with a phototransducer (e.g., a photomultiplier, a solid state array, a ccd camera, etc.) attached to an automated data acquisition system to automatically record the fluorescence signal produced by each nucleic acid enzyme on the array. Such automated systems are described at length in U.S. Pat. No. 5,143,854 and PCT application 20 92/10092.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain like or similar results without departing from the spirit and scope of the invention.

Example 1

In Vitro Selection of a Ion-Dependent Deoxyribozyme

This example demonstrates a method of creating nucleic acid enzymes that are dependent on the presence of an ion for activity. More specifically, use of a partially random DNA library to obtain deoxyribozymes that cleave RNA in the presence of $Zn^{2+}$ or $Co^{2+}$ is shown.

Materials and Methods Used in this Example

Oligonucleotides

DNA oligonucleotides were purchased from Integrated DNA Technologies Inc. Sequences of the random DNA template and the primers (P1, P2 and P3) used in PCR amplifications are listed below:

```
P1:
5'-GTGCCAAGCTTACCG-3'                  (SEQ ID NO: 3)

P2:
5'-CTGCAGAATTCTAATACGACTCACTATAGGAA    (SEQ ID NO: 4)

GAGATGGCGAC-3'

P3:
5'-GGGACGAATTCTAATACGACTCACTATrA-3'    (SEQ ID NO: 5)
```

Template for Random DNA Pool:

```
5'-GTGCCAAGCTTACCGTCAC-N40-GAGATCTC    (SEQ ID NO: 6)

GCCATCTCTTCCTATAGTGAGTCGTATTAG-3'
```

Primer P1b and P3b are the 5'-biotinylated version of primers P1 and P3. Primer P1a and P3a were prepared by 5'-labeling P1 and P3 with [γ-$^{32}$P] ATP (Amersham) and T4 polynucleotide kinase (Gibco). The DNA/RNA chimeric substrate (17DS) for trans-cleavage assays has the sequence 5'-ACTCACTATrAGGAAGAGATG-3' (SEQ ID NO:2), where rA denotes a single ribonucleotide. The all-RNA substrate (17RS) with the same sequence was purchased from Dharmacon Research Inc. The trans-cleaving deoxyribozyme 17E has the sequence 5'-CATCTCTTCTCCGAGCCGGTCGAAATAGTGAGT-3' (SEQ ID NO:1). The deoxyribozyme named 17E1 is a variant of 17E with the sequence 5'-CATCTCTTTTGTCAGCGACTCGAAATAGTGA GT-3' (SEQ ID NO:7). All oligonucleotides were purified using denaturing polyacrylamide gel electrophoresis and desalted with the SepPak nucleic acid purification cartridges (Waters) before use.

Preparation of Random DNA Pool

The initial pool for DNA selection was prepared by template-directed extension followed by PCR amplification. The extension was carried out with 200 pmol of DNA template containing a 40-nucleotide random sequence region, and 400 pmol of primer P3b in 20×100 μl reaction mixtures for four thermal-cycles (1 min at 92° C., 1 min at 52° C., and 1 min at 72° C.). Reaction buffer also included 0.05 U/μl Taq polymerase (Gibco), 1.5 mM $MgCl_2$, 50 mM KCl, 10 mM Tris-HCl (pH 8.3 at 25° C.), 0.01% gelatin and 0.2 mM of each dNTP. Subsequently, 1 nmol each of P1 and P3b were added to the extension product to allow four more cycles of PCR amplification. The products were precipitated with ethanol and dissolved in 0.5 ml of buffer A, which contains 50 mM HEPES (pH 7.0), 500 mM (for Zn-DNA selection) or 1 M (for Co-DNA selection) NaCl. About 20 μM EDTA was also added to the buffer to chelate trace amount of divalent metal ion contaminants.

In Vitro Selection

The random DNA pool was immobilized on a NeutrAvidin column (Pierce) by incubating with the column materials for 30 minutes. The mixture was gently vortex-mixed a few times during the incubation. The unbound DNA strands were eluted with at least 5×100 μl of buffer A. The non-biotinylated strands of immobilized DNA were washed off the column with 5×100 μl of freshly prepared 0.2 M NaOH and 20 μM EDTA. The column was then neutralized with 5×100 μl of buffer A The cleavage reaction was carried out by incubating the immobilized single-stranded DNA containing the single ribonucleotide (rA) with 3×20 μl of reaction buffer (buffer A plus 1 mM $ZnCl_2$ or $CoCl_2$) over 1 h. The eluted DNA molecules were pooled and precipitated with ethanol. A fraction of the selected DNA was amplified in 100 μl PCR reaction with 40 pmol each of primers P1 and P2 over 10–20 thermal cycles. One tenth of the PCR product was further amplified for six cycles with 50 pmol of primers P1 and P3b. The final PCR product was ethanol precipitated and used to initiate the next round of selection. During the selection of Zn(II)-dependent deoxyribozymes (called Zn-DNA hereafter), the concentration of $ZnCl_2$ was kept constant at 100 μM in the reaction buffer for the following rounds of selection. Reaction time was gradually decreased from 1 h to 30 s within 12 rounds of selection. For the selection of Co(II)-dependent deoxyribozymes (called Co-DNA hereafter), the concentration of $CoCl_2$ was gradually decreased from 1 mM to 100 μM and the reaction time from 1 h to 1 min within 10 rounds of selection. The twelfth generation of selectively amplified Zn-DNA and the tenth generation of Co-DNA were cloned using TA-TOPO Cloning Kit (Invitrogen) and sequenced with T7 Sequenase 2.0 Quick-denatured Plasmid Sequencing Kit (Amersham).

Reselection

Based on the sequence of class I Zn-DNA or Co-DNA, partially degenerate DNA template libraries for reselection were synthesized (Integrated DNA Technology Inc.) with 20% degeneracy at the N40 region. In other words, during the oligonucleotide synthesis of the N40 region, the wild type sequence was introduced at a probability of 80% at each position, while the other three nucleotides each occurred at a probability of 6.67%. The reselection pool was prepared with 10 pmol of template and 100 pmol of primers P1 and P3b using the same protocol previously described. With 10 pmol (number of molecules $S=6\times10^{12}$) of partially randomized template, the statistic parameters of the DNA library used for reselection were calculated based on the following equations.

$$P(k,n,d)=[n!/(n-k)!k\,!]d^k(1-d)^{n-k} \quad (1)$$

$$N(k)=[n!/(n-k)!k!]3^k \quad (2)$$

$$C(n,k)=SP(k,n,d)/N(k) \quad (3)$$

P(k,n,d) is the probability of having k mutations within n (number of randomized positions, n=40) nucleotide positions that have been randomized at a degeneracy of d. N(k) is the number of distinct sequences that have k mutations with respect to the prototype sequence. C(n,k) is the number of copies for each sequence that has k mutations. The reselection pool was expected to contain the wild type sequence, all possible sequences with 1–8 point mutations, and a sampling of the sequences with >8 point mutations. More than half of the population contains ≧8 point-mutations. The protocol for reselection was the same as the primary selection, except that the reaction time was decreased from 20 min to 1 min and the concentration of $ZnCl_2$ or $CoCl_2$ was decreased from 20 µM to 5 µM over six generations. The sixth generation of reselected Zn- or Co- DNA were cloned and sequenced as previously described.

Kinetic Assays of the Reselected Cis-Cleaving DNA

The 5' $^{32}$P-labeled precursor DNA for cis-cleavage assay was prepared by PCR-amplification of the selected DNA population or the cloned DNA plasmid with primer 1b and 3a. The double-stranded product was immobilized on a NeutrAvidin column through the biotin moiety on primer P1b. The catalytic strand of DNA was eluted off the column with 3×20 µl freshly prepared 0.2 N NaOH and neutralized with 8 µl of 3 M sodium acetate (pH 5.3) in the presence of 50 µg/ml bovine serum albumin (Sigma). Following ethanol precipitation, the single-stranded DNA was purified on an 8% denaturing polyacrylamide gel and desalted with SepPak nucleic acid purification cartridge. Bovine serum albumin (50 µg/ml) was added to the gel-soaking buffer (0.2 M NaCl, 20 µM EDTA, 10 mM Tris-HCl, pH 7.5) to prevent the DNA from adhering to the tube. The concentration of the DNA was determined by scintillation counting the radioactivity.

The precursor DNA was dissolved in buffer A and incubated at room temperature for 10 min before $CoCl_2$ or $ZnCl_2$ was added. The reaction was stopped with 50 mM EDTA, 90% formamide and 0.02% bromophenol blue. Reaction products were separated on an 8% denaturing polyacrylamide gel and quantified with a Molecular Dynamic phosphorimager.

In vitro Selection of Zn(II)- or Co(II)-Dependent Deoxyribozymes

The DNA molecules capable of cleaving an RNA bond in the presence of $Co^{2+}$ or $Zn^{2+}$ were obtained through in vitro selection. The initial DNA library for selection contains ~$10^{14}$ out of the possible $10^{24}$ (=$4^{40}$) DNA sequences. These molecules consist of a random sequence domain of 40 nucleotides flanked by two conserved primer-binding regions. The sequence of the conserved region was designed in such a way that they could form two potential substrate-binding regions (FIG. 1A). A ribonucleic adenosine was embedded in the 5'-conserved sequence region and was intended to be the cleavage site, since an RNA bond is more susceptible than a DNA bond toward hydrolytic cleavage. The intrinsic half-life of the phosphodiester linkage in RNA at pH 7 and 25° C. is estimated to be 1,000 years. The corresponding value for DNA is 200 million years.

Figure 1B:
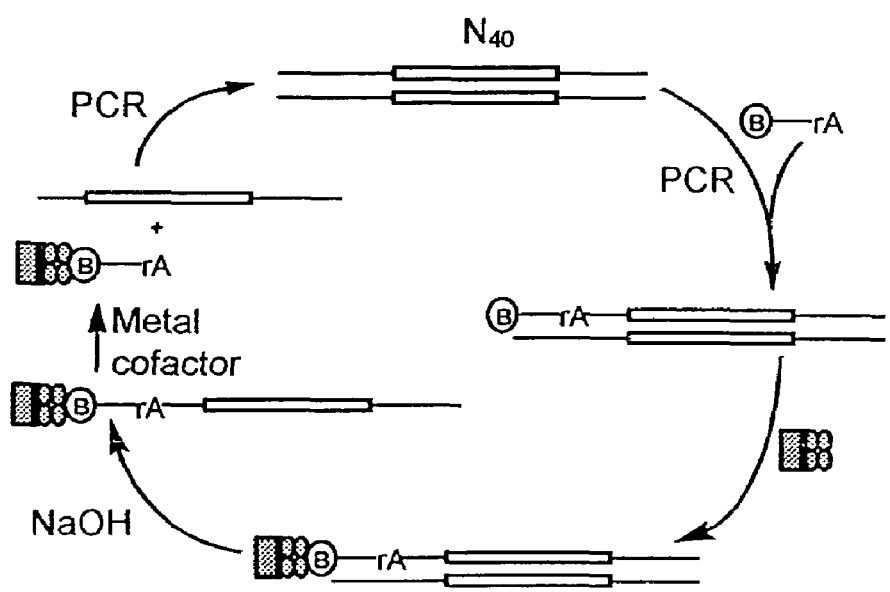
FIG. 1B. Selective amplification scheme for isolation of DNA that catalyzes the metal cofactor ($Co^{2+}$ or $Zn^{2+}$) dependent cleavage of an RNA phosphodiester.

The DNA pool was immobilized on a NeutrAvidin column through the biotin moiety on the 5' terminus of the DNA. Biotin and Avidin bind strongly with an association constant of $K_a=10^{15}$ $M^{-1}$. The sequences that underwent self-cleavage in the presence of $Co^{2+}$ or $Zn^{2+}$ were eluted off the column, amplified and used to seed the next round of selection (FIG. 1B). The selection stringency was increased during the selection process with shorter reaction time and less available divalent metal ions. The activity of the selected Zn-DNA gradually increased until the twelfth generation and declined thereafter, while the highest activity was achieved with the tenth generation of Co-DNA. Therefore the twelfth generation of Zn-DNA and the tenth generation of Co-DNA were cloned and sequenced. The cloned sequences can be divided into different classes based on sequence similarity (FIG. 2 and FIG. 3).

Individual sequences of the cloned Zn-DNA and Co-DNA were randomly chosen and sampled for activity. Under the selection conditions (100µM $Zn^{2+}$, 500 mM NaCl, 50 mM HEPES, pH 7.0 25° C.), the observed rate constants of Zn-DNAs from sequence-classes I and II were 0.1–0.2 $min^{-1}$, while class III sequences were less active, with $k_{obs}$ around 0.02 $min^{-1}$. The cleavage rate of the initial pool was $2\times10^{-7}$ $min^{-1}$. Therefore, a $10^5$-$10^6$ fold increase in cleavage rate has been achieved for Zn-DNA selection. The cleavage rates of all the randomly picked Co-DNA sequences were <0.02 $min^{-1}$ under the conditions for Co-DNA selections (100 µM $Co^{2+}$, 1 M NaCl, 50 mM HEPES, pH 7.0, 25° C.). Interestingly, even in the buffer (1 M NaCl, 50 mM HEPES, pH 7.0) alone, the class II Co-DNA exhibited similar activity as in the presence of 100 µM $Co^{2+}$or $Zn^{2+}$.

Clone #5 of Zn-DNA (Zn-5) and clone #18 of Co-DNA (Co-18) showed relatively high activity, as well as high frequency of occurrence, within their lineages. The $k_{obs}$ were 0.17 $min^{-1}$ for Zn-5 (in 100 µM $Zn^{2+}$) and 0.02 $min^{-1}$ for Co-18 (in 100 µM $Co^{2+}$). The sequences of Zn-5 and Co-18 were partially randomized (see Material and Methods for details) and subjected to reselection in order to further improve the reactivity and metal-binding affinity, and to explore the sequence requirement of the conserved catalytic motif Based on equations (1)–(3), the reselection pool was expected to contain the wild type sequence, all possible sequences with 1–8 point mutations, and a sampling of the sequences with >8 point mutations. More than half of the population should contain ≧8 point mutations. Six rounds of reselection were carried out with 5–20 µM $Zn^{2+}$ or $Co^{2+}$, however the activity of the reselected DNA was similar to the activity of the wild type sequences. Sequencing of the Zn-DNA from both the initial selection and reselection revealed a highly conserves sequence region. Therefore the lack of activity improvement after reselection likely reflects a sequence pool dominated by a few highly reactive sequences.

Sequence Alignment and Structure Analysis of Zn-DNA

The sequences of thirty individual clones of initially selected Zn-DNA can be divided into three major classes based on sequence similarity. Differences among members of each class were limited to a few point mutations (FIG. 2). A highly conserved sequence region of 20 nt, 5'-T$X_1X_2X_3$AGC$Y_1Y_2Y_3$TCGAAATAGT-3' (SEQ ID NO:8) (Region-20nt), was observed in all but one sequence albeit at different locations. The sequences of 5'-$X_1X_2X_3$-3' and 3'-$Y_3Y_2Y_1$-5'are complimentary and covariant, indicating that they form base pair with each other:

5'-$X_1X_2X_3$-3'
3'-$Y_3Y_2Y_1$-5'

The secondary structures of the sequenced Zn-DNA were predicted using Zuker's DNA mfold program (see http://mfold.wustl.edu/~folder/dna/form1.cgi) through minimization of folding energy. The most stable structures predicted for those containing Region-20nt all contained a similar structure motif This common motif consists of a pistol-shaped three-way helical junction formed by a 3 bp hairpin, an 8 bp hairpin and a double helix linking to the rest of the molecule. The 3 bp hairpin and its adjacent single-stranded regions are part of the Region-20nt. The ribonucleic adenosine is unpaired and positioned opposite of the 3 bp hairpin.

Figure 4:
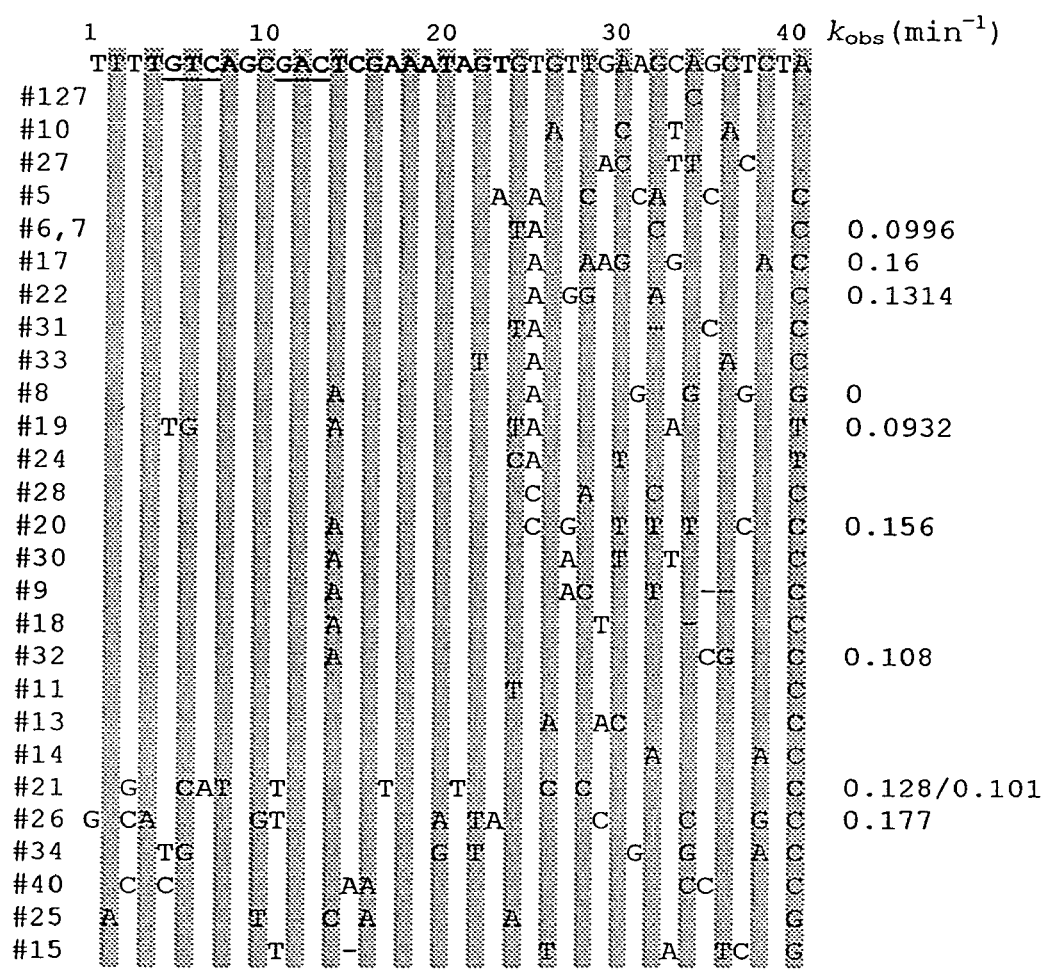
FIG. 4. (SEQ ID NOS 43–70, respectively, in order of appearance) Sequence alignment of the N40 region of the reselected Zn-DNAs. The wild-type sequence is listed on the top, followed by the reselected Zn-DNA sequences. Only the point mutations are shown for the reselected sequences, while the nucleotides that are identical to the wild type at the corresponding positions are omitted. Numbers listed to the left are clone-numbers. The rate constants ($k_{obs}$) of several reselected Zn-DNA in 100 µM $Zn^{2+}$ are shown on the right.

After reselection, twenty-eight Zn-DNA clones were sequenced (FIG. 4). When compared with the parental wild type sequence (class I Zn-DNA), the reselected Zn-DNA contained point mutations mostly outside of Region-20nt. About one third of these sequences have a T→A mutation at position 73, converting the T—T mismatch in the wild type sequence to a Watson-Crick base pair. In one fourth of the reselected DNAs, the 5 nucleotide single-stranded bulge of the three-way junction has the sequence 5'-ACGAA-3', corresponding to 5'-TCGAA-3' in the wild type. Clone #17 (named ZnR17) of the reselected Zn-DNA is most active under selection conditions (FIG. 4). Structural analysis of ZnR17 revealed two completed base-paired helices in the three-way junction. Therefore, it was engineered into a trans-cleaving deoxyribozyme by deleting the sequences outside of the three-way junction and the loop of the 8 bp hairpin. Such truncation resulted in two individual stands, which hybridize with each other through two 9–10 bp helices. The strand containing the single ribonucleotide residue (rA) is considered as the substrate (named 17DS), while the other strand as the enzyme (named 17E). The catalytic core, which was highly conserved during selection, consists of a 3 bp hairpin and a 5 nt single-stranded bulge (FIG. 5).

Although ZnR17 was selected in $Zn^{2+}$, it does not contain structure motifs that were discovered in several Zn(II)-binding RNA molecules (Ciesiolka et al., 1995; Ciesiolka & Yarus, 1996). However, the conserved region of ZnR17 is very similar to that of the 8-17 deoxyribozymes selected by Santoro and Joyce using $Mg^{2+}$ as cofactor (Santoro & Joyce, 1997). The unpaired bulge region in the 8-17 DNA enzyme has the sequence 5'-WCGR-3' or 5'-WCGAA-3' (W=A or T; R=A or G). The highest activity was observed with the sequence containing 5'-TCGAA-3'. Among the Zn(II)-dependent deoxyribozymes we obtained after reselection, 85% of them fell within the 5'-WCGAA-3' regime (W=A or T). However, the sequence of the two double helices flanking the catalytic core is different between the 8-17 (FIG.y 6D) and the 17E deoxyribozymes (FIG. 6F), reflecting their different designs of the selection pool. Similar sequence motif was also observed in an RNA-cleaving deoxyribozyme (named Mg5) selected by Faulhammer and Famulok using 50 mM histidine and 0.5 mM $Mg^{2+}$ as cofactors (Faulhammer & Famulok, 1997). The homologous region in 31 out of the 44 sequenced clones had the sequence 5'-$TX_1X_2X_3AGCY_1Y_2Y_3ACGAA$-3' (SEQ ID NO:9), falling within the WCGAA-3' regime. The authors predicted a secondary structure different from the 8-17 or 17E motif based on chemical modification analysis. However, a structure containing a three-way junction similar to that of the 17E and 8-17 deoxyribozymes is consistent with the chemical mapping results.

Sequence Alignment and Structure Analysis of Co-DNA

The sequences of the cis-cleaving deoxyribozyme selected in the presence of $Co^{2+}$ are more diverse than the Zn-DNA. They can be divided into three major classes based on sequence similarity (FIG. 3). There is no consensus sequence region among different classes. The secondary structure of each sequence class of Co-DNA was predicted with DNA mfold program. The minimal conserved sequence motif of class I Co-DNA includes a bulged duplex. The cleavage site is within the 13 nt single-stranded bulge. A 4 bp hairpin is also highly conserved and linked to the bulged duplex through 3 unpaired nucleotides. The folding of the sequences outside of this minimal motif was highly variable and resulted in structures with a wide range of stabilization energy.

Figure 7A:
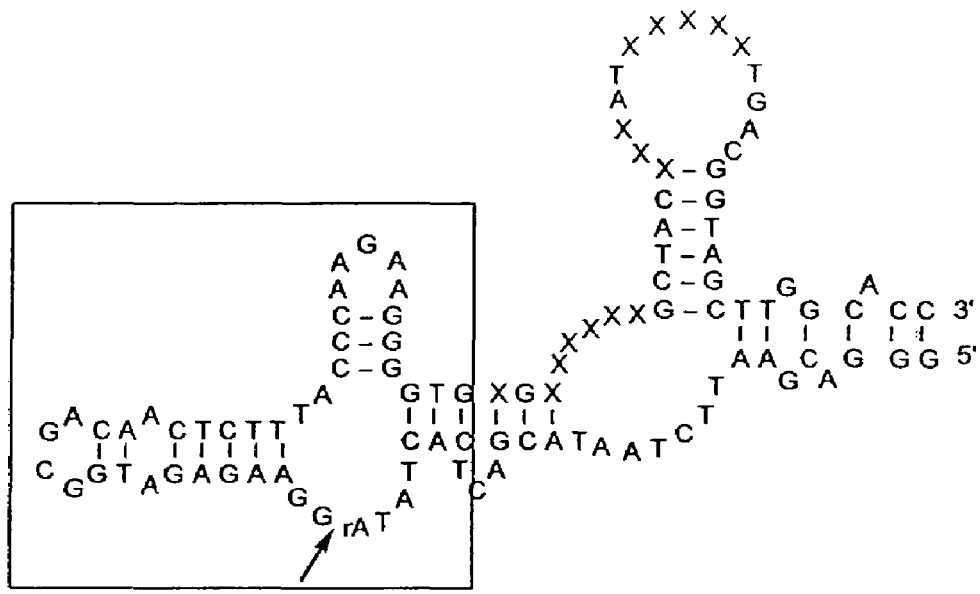
FIG. 7A. (SEQ ID NO 83) The predicted secondary structure of the G3 deoxyribozyme (Geyer & Sen, 1997). X represents variable sequences. The boxed region was also found in class II Co-DNA.
Figure 7B:
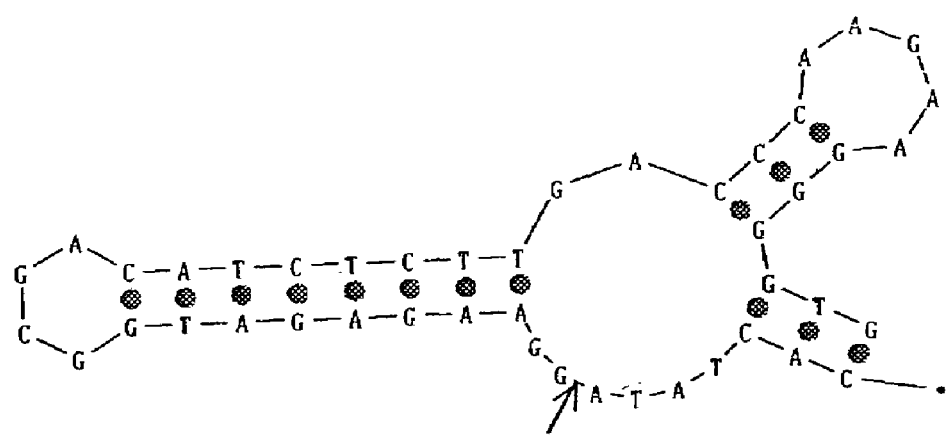
FIG. 7B. (SEQ ID NO 84) The minimal structure motif of the class II Co-DNA predicted by mfold program. The arrows indicate the cleavage sites.

The class II Co-DNA contains a sequence region (5'-ACCCAAGAAGGGGTG-3' (SEQ ID NO:10)) that was also found in an RNA-cleaving deoxyribozyme (termed G3) selected by Geyer and Sen (1997) (FIGS. 7A and 7B). The minimal motif predicted for class II Co-DNA shows similarity to that proposed for the G3 deoxyribozyme as well. The G3 deoxyribozyme was believed to be fully active in the absence of any divalent metal ions. Copious use of divalent metal chelating agents, such as EDTA, and accurate trace-metal analysis of the reaction solutions were used to rule out the need of the G3 deoxyribozyme for contaminating levels of divalent metals. As mentioned earlier, the activity of class II Co-DNA was the same in buffer alone or with added $Co^{2+}$ or $Zn^{2+}$, suggesting that this class of Co-DNA most likely contain the divalent metal-independent structure motif Effect of Metal Ions on the Activity of the Cis-Cleaving Deoxyribozymes ZnR17 and Co-118 were examined for their activity dependence on monovalent ions and divalent metal ions other than $Zn^{2+}$ and $Co^{2+}$. In the presence of 1 mM EDTA and without added $Zn^{2+}$ ions, no cleavage was observed with ZnR17 even after two days, strongly suggesting that divalent metal ions are required for the activity of ZnR17. Although the cis-cleaving Zn-DNA was selected in the presence of 500 mM NaCl, NaCl was actually inhibitory to enzymatic activity. With 0–2 M NaCl added to the reaction buffer (100 µM $Zn^{2+}$, 50 mM HEPES, pH 7.0), $k_{obs}$ decreased with increasing NaCl concentration. The deleterious effect of NaCl was also manifested by lowered final percentage of cleavage products. For instance, only 50% of ZnR17 could be cleaved in the presence of 2 M NaCl even after long incubation times, while >95% of the DNA was cleavable in the absence of extra NaCl. Contrary to the Zn-DNA, the activity of Co-18 relies on NaCl and no cleavage was observed in the absence of NaCl. With 1 M NaCl, 8% of Co-18 molecules were cleaved within 5 min, while <0.2% were cleaved in the absence of extra NaCl.

Although the deoxyribozymes were selected using either zinc or cobalt as cofactor, they are also active in other transition metal ions and in $Pb^{2+}$. The cleavage efficiency of ZnR17 followed the trend of $Pb^{2+}>Zn^{2+}>Mn^{2+}\sim Co^{2+}\sim Ca^{2+}>Cd^{2+}>>Ni^{2+}>Mg^{2+}$. It is noteworthy that the cleavage rate in $Ca^{2+}$ was much higher than in $Mg^{2+}$, a similar trend was observed with the Mg5 deoxyribozyme. The order of Co-18 activity is as follow: $Zn^{2+}>Pb^{2+}\sim Co^{2+}\sim Ni^{2+}>Cd^{2+}\sim Mn^{2+}>M^{2+}\sim Ca^{2+}$. In general, both ZnR17 and Co-18 are more active in transition metal ions than in alkaline-earth metals, and higher activities were achieved with $Pb^{2+}$, $Co^{2+}$ and $Zn^{2+}$. The preference of the selected deoxyribozymes for $Co^{2+}$ and $Zn^{2+}$ reflected their selection criteria. A similar trend ($Pb^{2+}>Zn^{2+}>Mn^{2+}>Mg^{2+}$) was also observed with all four RNA-cleaving deoxyribozymes selected in parallel by Breaker and Joyce using one of the four metal ions ($Pb^{2+}$, $Zn^{2+}$, $Mn^{2+}$, $Mg^{2+}$) as cofactor (1995). The proposed secondary structures of the deoxyribozymes selected in $Pb^{2+}$ and $Mg^{2+}$ have been reported (Breaker & Joyce, 1994, 1995). No structure similarity was observed between ZnR17 and those RNA-cleaving deoxyribozymes.

SUMMARY

Using in vitro selection technique, several groups of RNA-cleaving deoxyribozymes were isolated using $Zn^{2+}$ or $Co^{2+}$ as cofactor. No common sequence or structural features were observed between the Co(II)-dependent and the Zn(II)-dependent deoxyribozymes, in spite of the chemical similarities between these two transition metal ions. The deoxyribozymes selected in $Zn^{2+}$ share a common motif with the 8-17 and the Mg5 deoxyribozymes isolated under different conditions, including the use of different cofactors. Both the Co-DNA and the Zn-DNA exhibited higher activity in the presence of transition metal ions than in alkaline earth metal ions, which are the most commonly adopted metal cofactors by naturally occurring ribozymes.

Example 2

Deoxyribozyme as a Biosensor for $Pb^{2+}$ Detection

This Example describes a fluorescence-based biosensor for the detection of $Pb^{2+}$. The biosensor utilizes a deoxyribozyme developed in Example 1 (termed 17E) combined with fluorescence technology to allow quantitative and real time measurements of catalytic activity. Because catalytic activity is dependent on $Pb^{2+}$, the biosensor provides real-time, quantitative, and sensitive measurements of $Pb^{2+}$ concentrations.

Materials and Methods used in this Example

Oligonucleotides

The oligonucleotides were purchased from Integrated DNA Technology Inc. The cleavable substrate (Rh-17DS) is a DNA/RNA chimera with the sequence 5'-ACTCAC-TATrAGGAAGAGATG-3' (SEQ ID NO:2), in which rA represents a ribonucleotide adenosine. This RNA base is replaced with a DNA base for the non-cleavable substrate (Rh-17DDS) (SEQ ID NO:11) used in the control experiment. Both substrates are covalently linked at the 5' end with 6-carboxytetramethylrhodamin through NHS-ester conjugation. The deoxyribozyme (17E-Dy) is labeled at the 3'-end with Dabcyl via CPG phosphoramidite and has the sequence 5'-CATCTCTTCTCCGAGCCGGTCGAAATAGTGAGT-3' (SEQ ID NO:1). All the oligonucleotides were purified by denaturing 20% polyacrylamide gel electrophoresis to ensure 100% labeling with the fluorescent dyes.

Fluorescence Spectroscopy

The enzyme-substrate complex was prepared with 50 nM each of 17E-Dy and Rh-17DS in 50 mM NaCl, 50 mM HEPES (pH 7.5) with a volume of 600 μl. The sample was heated at 90° C. for 2 min and cooled to 5° C. over 15 min to anneal the enzyme and substrate strands together. Steady-state and slow kinetic fluorescence spectra were collected with a SLM 8000S photon counting fluorometer. Polarization artifacts were avoided by using "magic angle" conditions. The steady-state emission spectra were collected from 570 to 700 nm ($\lambda_{ex}$=560 nm). The time-dependent DNA enzyme catalyzed substrate cleavage was monitored at 580 nm at 2 s intervals. To initiate the reaction, 1–2 μl of concentrated divalent metal ion solution was injected into the cuvette using a 10 μl syringe while the DNA sample in the cuvette was constantly stirred.

DNA-Based Sensor of Metal Ions

An in vitro selected DNA enzyme from Example 1 (termed 17E) that is capable of cleaving a lone RNA linkage within a DNA substrate (termed 17DS) (FIG. 5) was chosen for use as a DNA-based, fluorescent biosensor of metal ions. Assays of this enzyme indicate a highly $Pb^{2+}$ dependent activity with $k_{obs}$=6.5 $min^{-1}$ at pH 6.0 and $K_{apparent}$=13.5 $\mu M^{35}$. The fluorosensor was constructed by labeling the 5'-end of the substrate with the fluorophore 6-carboxytetramethylrhodamin (TAMRA) and the 3'-end of the enzyme strand with 4-(4'-dimethylaminophenylazo)benzoic acid) (Dabcyl). Dabcyl serves as a universal fluorescence quencher. Steady-state fluorescence spectra were obtained by exciting the sample at 560 nm and scanning its emission from 570 to 700 nm.

When the substrate (Rh-17DS) was hybridized to the enzyme strand (17E-Dy), the fluorescence of TAMRA was quenched by the nearby Dabcyl (FIG. 8). Upon addition of $Pb^{2+}$, this quenching was eliminated and the fluorescence of TAMRA increased by ~400%. Little change in the fluorescence signal occurred with addition of $Pb^{2+}$ to the substrate alone or to the complex of the enzyme and a non-cleavable all DNA substrate with identical sequence. These findings show that the change in fluorescent signal with Rh-17DS/17E-Dy results from a DNA enzyme-catalyzed substrate cleavage, followed by product release.

Figure 9A:
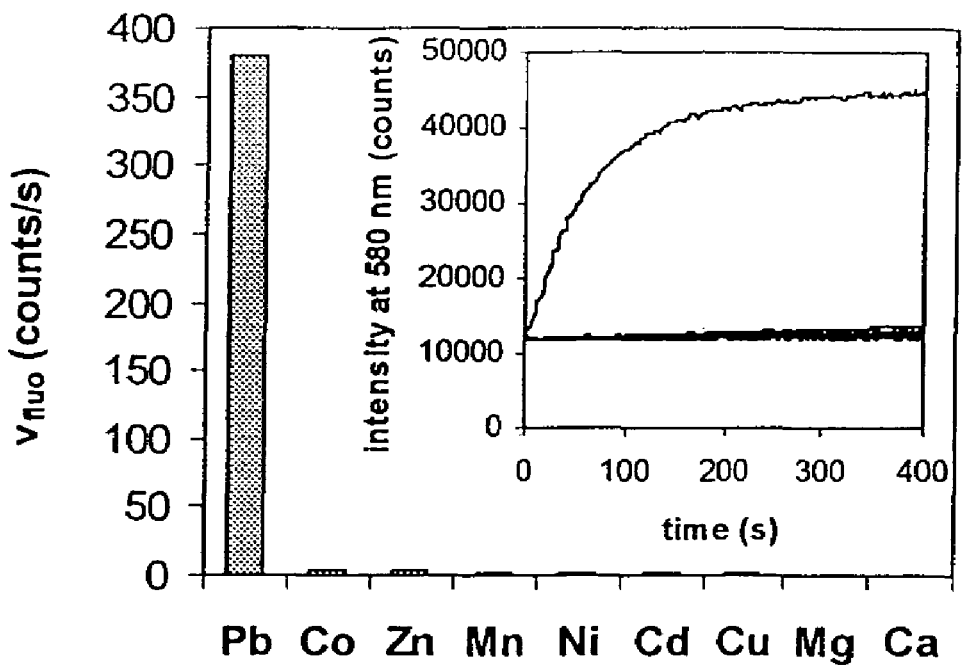
FIG. 9A. with 500 nM M(II) in 50 mM HEPES (pH 7.5); The inserted graph shows the change of fluorescence intensity at 580 nm in response to the addition of M(II). The curve with dramatic change was collected in Pb(II), the other curves were collected in one of the other eight divalent metal ions.
Figure 9B:
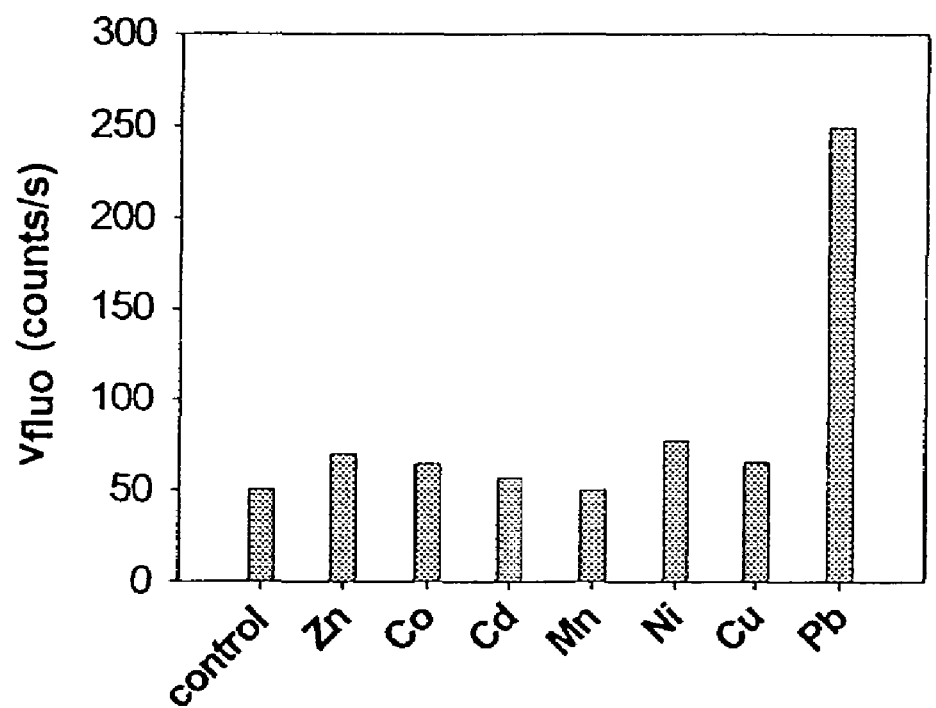
FIG. 9B. with 500 nM M(II) in 100 mM NaCl, 1 mM $Mg^{2+}$, 1 mM $Ca^{2+}$ and 50 mM HEPES (pH 7.5).

The substrate cleavage reaction was monitored in real time with fluorescence spectroscopy. Like the ratiometric, anisotropy, or lifetime-based method, kinetic fluorescence measurement is independent of sampling conditions such as illumination intensity and sample thickness (Oehme & Wolfbeis, 1997). In order to determine the selectivity of the catalytic DNA sensor, the fluorescence change ($\lambda$=580 nm, $\lambda_{ex}$=560 nm) of Rh-17DS/17E-Dy upon addition of nine different divalent metal ions that are known to be active toward DNA/RNA cleavage (FIG. 9A) was monitored. At the same concentration, $Pb^{2+}$ caused the most rapid change in fluorescence with a rate of 380 counts·$s^{-1}$ at 500 nM $Pb^{2+}$, pH 7.5. The sensitivity toward $Pb^{2+}$ was >80 times higher than other divalent metal ions (FIG. 9A). Remarkably, this trend of selectivity was maintained even under simulated physiological conditions containing 100 mM NaCl, 1 mM $Mg^{2+}$, and 1 mM $Ca^{2+}$ (FIG. 9B). Furthermore, the signal response to $Pb^{2+}$ was not affected by the presence of equal amounts of each of these divalent metal ions. Therefore, this DNA enzyme sensor is well suited for selective monitoring $Pb^{2+}$ in the presence of other metal ions.

Figure 10A:
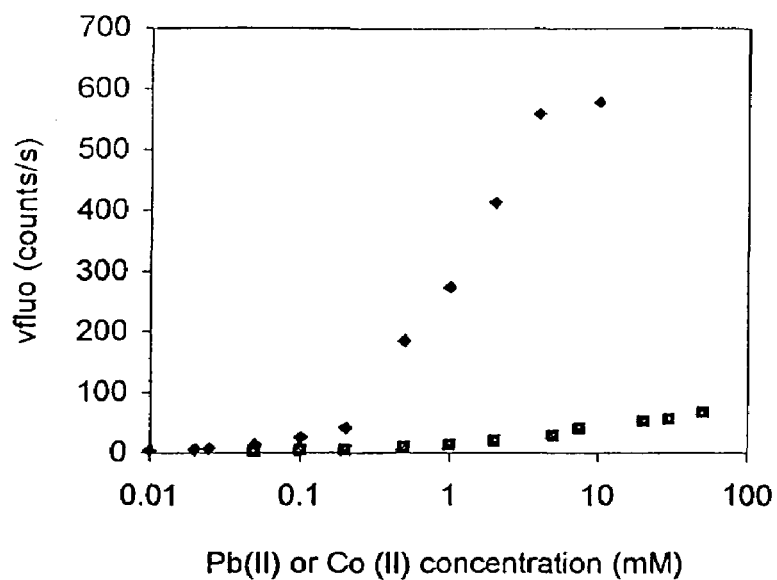
FIG. 10A. The initial rate ($v_{fluo}$) increased with the concentration of $Pb^{2+}$ (♦) and $Co^{2+}$ (■) over a range of three orders of magnitude.
Figure 10B:
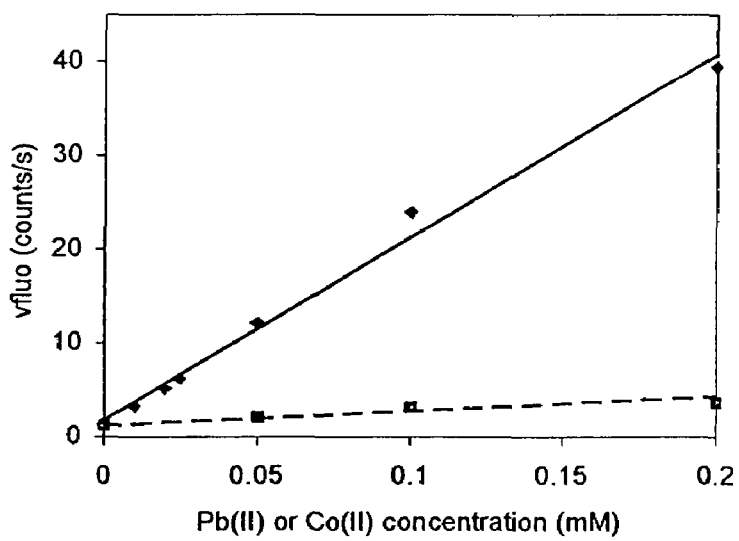
FIG. 10B. At low concentrations, $v_{fluo}$ increased linearly with $Pb^{2+}$ (♦) or $Co^{2+}$ (■) concentration.

In addition to the selectivity of the DNA enzyme probe for $Pb^{2+}$ over other metal ions, the range of $Pb^{2+}$ concentrations which give rise to a fluorescent response is also important. As shown in FIG. 10A, the rate of fluorescence change increased with $Pb^{2+}$ concentration up to 4 μM. The detection limit for $Pb^{2+}$ is around 10 nM, 50 fold less than the toxic level defined by the Center for Disease Control.

Example 3

DNA Chip Comprising an Array of Nucleic Acid Enzymes

This prophetic example describes the production of and use of a DNA chip for sensing ions, in particular heavy metal ions.

The first step towards the application of deoxyribozymes in heavy metal sensing is to obtain various deoxyribozymes with different metal specificity and affinity. In vitro selection will be carried out to isolate a variety of deoxyribozymes. A detailed description of the selection protocol can be found in Example 1. Each family of deoxyribozyme will be specific for different divalent metal ions (e.g. $Pb^{2+}$, $Hg^{2+}$, $Zn^{2+}$, $Co^{2+}$, $Cd^{2+}$, $Ni^{2+}$, $Mn^{2+}$, etc). Within each family, different sequences will have different affinities of the specified metal ion.

Figure 11B:
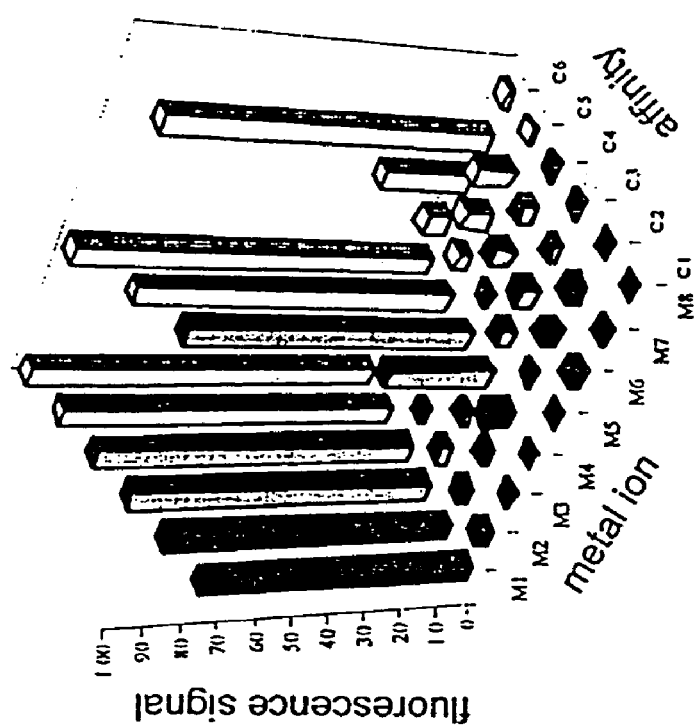
FIG. 11B. Quantitative and qualitative detection of metal ions using the metal ion-sensing deoxyribozyme chip. The z-axis represents the fluorescence intensity change upon the exposure of the chip to the sample under examination. The change in the fluorescence intensity is caused by the deoxyribozyme-catalyzed substrate cleavage in the presence of a specific kind and concentration of metal ion.
Figure 11A:
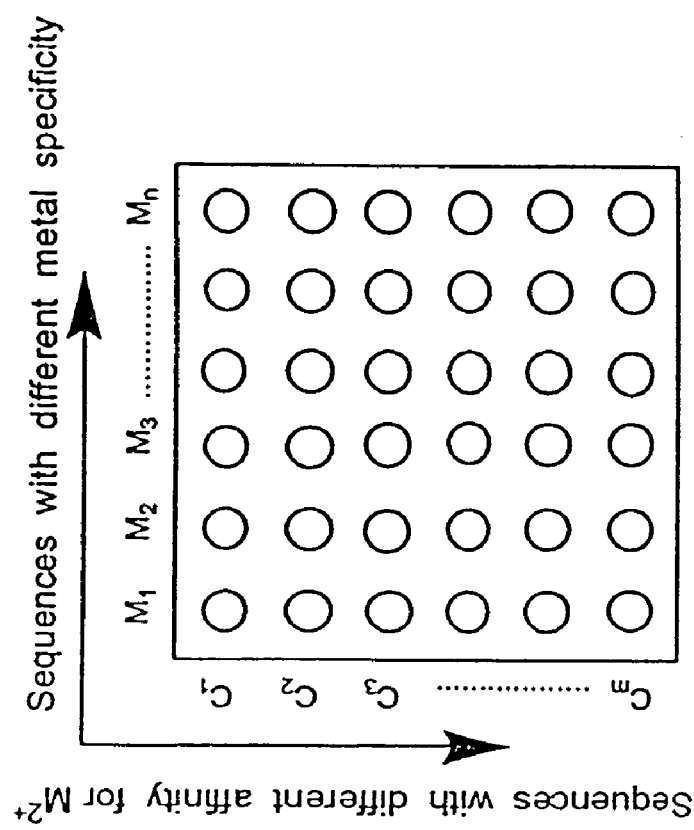
FIG. 11A. The array of deoxyribozymes with different metal specificity and affinity on the DNA chip for metal ion sensing.

These deoxyribozymes and their substrates will then be arrayed onto a DNA chip with one dimension for metal ion specificity and the other for affinity of the corresponding metal (FIG. 11). The enzyme strands immobilized on the chip at 3'-ends can be synthesized on the chip using photolithographic methods (Fodor et al., 1991; Pease et al., 1994) or can be synthesized off-chip and then attached to the chip using various methods (Joos et al., 1997; O'Donnell-Maloney et al., 1997; Guschin et al., 1997). The 5'-end of the enzyme strand will be labeled with a fluorophore. The 3'-end of the substrate strand will be labeled with a fluorescence quencher, which can be a fluorescent or non-fluorescent moiety. For example, guanidine base is an efficient quencher of fluorescein.

Hybridization of the enzyme and substrate will result in the quenching of the donor fluorescence. Upon exposure to the sample containing the active metal ion, the substrate will be cleaved and products will dissociate, resulting in strong fluorescence of the dye attached to the enzyme strand. The metal ion species can be qualitatively identified based on the metal specificity of different families of deoxyribozymes. A hypothetical sample result is shown in FIG. 11B. The pattern of fluorescence intensity shows that there are three kinds of metal (M1, M4, and M6) in the sample.

The concentration of the metal ion under inspection can be quantified with deoxyribozymes with different metal affinity. Given a certain concentration of the metal ion, different sequences within the same family will have different cleavage efficiencies due to their different threshold in response to the metal concentration. The metal concentration applied may exceed the saturation concentration of those having higher affinity; therefore full cleavage will occur within a certain time and present strong fluorescence. On the other hand, the substrates of those with lower affinity will only be partly cleaved and emit weaker fluorescence. The sample hypothetical result shown in FIG. 11B shows high (c1), medium (c4), and low (c6) concentrations of M1, M4, and M6, respectively.

The fluorescence patterns with respect to different deoxyribozyme sequences will be compared with standard calibration maps. After de-convolution of the fluorescence pattern, direct information can be obtained about the identity and concentration of metal ions in the samples.

REFERENCES

Breaker, R. R.; Joyce, G. F. *Chem. Biol.* 1995, 2, 655–660.
Breaker, R. R. & Joyce, G. F. A DNA enzyme that cleaves RNA. *Chem. Biol.* 1, 223–229 (1994).
Breaker, R. R. DNA enzymes. *Nat. Biotechnol.* 15, 427–431 (1997).
Cadwell, R. C.; Joyce, G. F. *PCR Methods Appl.* 1992, 2, 28–33.
Cadwell, R. C.; Joyce, G. F. *PCR Methods Appl.* 1994, 3, S136–S140.
Carmi, N., Shultz, L. A. & Breaker, R. R. In vitro selection of self-cleaving DNAs. *Chem. Biol.* 3, 1039–1046 (1996).
Chapman, K. B.; Szostak, J. W. *Curr. Opin. Struct. Biol.* 1994, 4, 618–622.
Ciesiolka, J.; Gorski, J.; Yarus, M. *RNA* 1995, 1, 538–550.
Ciesiolka, J.; Yarus, M. *RNA* 1996, 2, 785–793.
Conaty, J.; Hendry, P.; Lockett, T. *Nucleic Acids Res.* 1999, 27, 2400–2407.
Conn, M. M.; Prudent, J. R.; Schultz, P. G. *J. Am. Chem. Soc.* 1996, 118, 7012–7013.
Cuenoud, B. & Szostak, J. W. A DNA metalloenzyme with DNA ligase activity. *Nature* 375, 611–614 (1995).
Czarnik, A. W. Desperately seeking sensors. *Chem. Biol.* 2, 423–428 (1995).
Dai, X.; De Mesmaeker, A.; Joyce, G. F. *Science* 1995, 267, 237–240.
Deo, S. & Godwin, H. A. A Selective, Ratiometric Fluorescent Sensor for $Pb^{2+}$. *J. Am. Chem. Soc.* 122, 174–175 (2000).
Earnshaw & Gait, "Modified Oligoribonucleotides as site-specific probes of RNA structure and function," *Biopolymers* (John Wiley & Sons, Inc.) 48:39–55, 1998.
Ekland, E. H.; Szostak, J. W.; Bartel, D. P. *Science* 1995, 269, 364–370.
Ekland, E. H.; Bartel, D. P. *Nature* 1996, 382, 373–376.
Famulok, M. *Curr. Opin. Struct. Biol.* 1999, 9, 324–329.
Faulhammer, D.; Famulok, M. *Angew. Chem., Int. Ed Engl.* 1997, 35, 2837–2841.
Fodor, S. P. A., Read, J. L., Pirrung, M. C., Stryer, L., Lu, A. T. & Solas, D. (1991). Light-directed, spatially addressable parallel chemical synthesis. *Science* 251: 767–773.
Frank, D. N.; Pace, N. R. *Proc. Natl. Acad. Sci. U.S.A.* 1997, 94, 14355–14360.
Geyer, C. R.; Sen, D. *Chem. Biol* 1997, 4, 579–593.
Godwin, H. A. & Berg, J. M. A Fluorescent Zinc Probe Based on Metal-Induced Peptide Folding. *J. Am. Chem. Soc.* 118, 6514–6515 (1996).
Guschin, D., Yershov, G., Zaslavsky, A., Gemmell, A., Shick, V., Proudnikov, D., Arenkov, P. & Mirzabekov, A. (1997). Manual manufacturing of oligonucleotide, DNA, and protein microchips. *Anal. Biochem.* 250: 203–211.
Hennrich, G.; Sonnenschein, H.; Resch-Genger, U. *J. Am. Chem. Soc.* 1999, 121, 5073–5074.
Illangasekare, M.; Yarus, M. *J. Mol. Biol.* 1997, 268, 631–639.
Imperiali, B., Pearce, D. A., Sohna Sohna, J.-E., Walkup, G. & Torrado, A. Peptide platforms for metal ion sensing. *Proc. SPIE-Int. Soc. Opt. Eng.* 3858, 135–143 (1999).
Jhaveri, et al., Designed Signaling Aptamers that Transduce Molecular Recognition to Changes in Fluorescence Intensity, *Journal of the American Chemical Society*; 2000; 122(11); 2469–2473.
Joos, B., Kuster, H. & Cone, R. (1997). Covalent attachment of hybridizable oligonucleotides to glass supports. *Anal. Biochem.* 247: 96–101.
Joyce, G. F. *Curr. Opin. Struct. Biol.* 1994, 4, 331–336.
Koizumi, M.; Soukup, G. A.; Kerr, J. N. Q.; Breaker, R. R. *Nat. Struct. Biol.* 1999, 6, 1062–1071.
Lakowicz, J. R. In *Principles of Fluorescence Spectroscopy*; 2nd ed.; Kluwer Academic/Plenum: New York, 1999.
Lee, M., & Walt, D. R A fiber-optic microarray biosensor using aptamers as receptors. *Anal Biochem* 282(1):142–146, 2000.
Lehman, N.; Joyce, G. F. *Nature* 1993, 361, 182–185.
Li, J., Zheng, W., Kwon, A. H. & Lu, Y. In vitro selection and characterization of a highly efficient Zn(II)-dependent RNA-cleaving deoxyribozyme. *Nucleic Acids Res.* 28, 481–488 (2000).
Li, Y.; Sen, D. *Nat. Struct. Biol.* 1996, 3, 743–747.

Li, Y.; Breaker, R. R. *Proc. Natl. Acad. Sci. U.S.A.* 1999, 96, 2746–2751.

Li, Y.; Liu, Y.; Breaker, R. R. *Biochemistry* 2000, 39, 3106–3114.

Lohse, P. A.; Szostak, J. W. *Nature* 1996, 381, 442–444.

Lorsch, J. R.; Szostak, J. W. *Nature* 1994, 371, 31–36.

Miyawaki, A., et al. Fluorescent indicators for $Ca^{2+}$ based on green fluorescent proteins and calmodulin. *Nature* 388, 882–887 (1997).

O'Donnell-Maloney, M. J., Tang, K., Koester, H., Smith, C. L. & Cantor, C. R. (1997). High-Density, Covalent Attachment of DNA to Silicon Wafers for Analysis by MALDI-TOF Mass Spectrometry. *Anal. Chem.* 69: 2438–2443.

Oehme, I. & Wolfbeis, O. S. Optical sensors for determination of heavy metal ions. *Mikrochim. Acta* 126, 177–192 (1997).

Pan, T. & Uhlenbeck, O. C. A small metafloribozyrne with a two-step mechanism. *Nature* 358, 560–563 (1992).

Pan, T.; Dichtl, B.; Uhlenbeck, O. C. *Biochemistry* 1994, 33, 9561–9565.

Pearce, D. A.; Walkup, G. K.; Imperiali, B. *Bioorg. Med Chem. Lett.* 1998, 8, 1963–1968.

Pease, A. C., Solas, D., Sullivan, E. J., Cronin, M. T., Holmes, C. P. & Fodor, S. P. A. (1994). Light-generated oligonucleotide arrays for rapid DNA sequence analysis. *Proc. Natl. Acad. Sci. U.S.A.* 91: 5022–5026.

Piccirilli, J. A.; McConnell, T. S.; Zaug, A. J.; Noller, H. F.; Cech, T. R. *Science* 1992, 256, 1420–1424.

Pley, H. W.; Flaherty, K. M.; McKay, D. B. *Nature* 1994, 372, 68–74.

Potyrailo, R. A.; Conrad, R. C.; Ellington, A. D.; Hieftje, G. M. *Anal. Chem.* 1998, 70, 3419–3425.

Potyrailo, R. A., Conrad, R. C., Ellington, A. D. & Hieftje, G. M. (1999). Adapting Selected Nucleic Acid Ligands (Aptamers) to Biosensors. *Anal. Chem.* 70: 3419–3425.

Prudent, J. R.; Uno, T.; Schultz, P. G. *Science* 1994, 264, 1924–1927.

Robertson, M. P.; Ellington, A. D. *Nat. Biotechnol* 1999, 17, 62–66.

Robertson, M. P.; Ellington, A. D. *Nucleic Acids Res.* 2000, 28, 1751–1759.

Roth, A.; Breaker, R. R. *Proc. Natl. Acad. Sci. U.S.A.* 1998, 95, 6027–6031

Rurack, K., Kollmannsberger, M., Resch-Genger, U. & Daub, J. A Selective and Sensitive Fluoroionophore for HgI, AgI, and CuII with Virtually Decoupled Fluorophore and Receptor Units. *J. Am. Chem. Soc.* 122, 968–969 (2000).

Santoro, S. W.; Joyce, G. F. *Proc. Natl. Acad Sci U.S.A.* 1997, 94, 4262–4266.

Santoro, S. W., Joyce, G. F., Sakthivel, K., Gramatikova, S. & Barbas, C. F., III RNA Cleavage by a DNA Enzyme with Extended Chemical Functionality. *J. Am. Chem. Soc.* 122, 2433–2439 (2000).

Scott, W. G.; Finch, J. T.; Klug, A. *Cell* 1995, 81, 991–1002.

Tang and Breaker, *Proc. Natl. Acad. Sci. USA*, 97, 5784–5789 (2000).

Tarasow, T. M.; Tarasow, S. L.; Eaton, B. E. *Nature* 1997, 389, 54–57.

Thompson, R. B., Maliwal, B. P., Feliccia, V. L., Fierke, C. A. & McCall, K. Determination of Picomolar Concentrations of Metal Ions Using Fluorescence Anisotropy: Biosensing with a "Reagentless" Enzyme Transducer. *Anal. Chem.* 70, 4717–4723 (1998).

Tsang, J.; Joyce, G. F. *Methods Enzymol.* 1996, 267, 410–426.

Tsien, R. Y. Fluorescent and photochemical probes of dynamic biochemical signals inside living cells in *Fluorescenct Chemosensors for Ion and Molecule Recognization* (ed. Czarnik, A. W.) 13046 (American Chemical Society, Washington, D.C., 1993).

Tuerk, C.; Gold, L. *Science* 1990, 249, 505–510.

Uphoff, K. W.; Bell, S. D.; Ellington, A. D. *Curr. Opin. Struct. Biol.* 1996, 6, 281–288.

Vaish, N. K.; Heaton, P. A.; Fedorova, O.; Eckstein, F. *Proc. Natl. Acad. Sci. U.S.A.* 1998, 95, 2158–2162.

Walkup, G. K. & Imperiali, B. Design and Evaluation of a Peptidyl Fluorescent Chemosensor for Divalent Zinc. *J. Am. Chem. Soc.* 118, 3053–3054 (1996).

Wecker, M.; Smith, D.; Gold, L. *RNA* 1996, 2, 982–994.

Wiegand, T. W.; Janssen, R. C.; Eaton, B. E. *Chem. Biol.* 1997, 4, 675–683.

Wilson, C.; Szostak, J. W. *Nature* 1995, 374, 777–782.

Winkler, J. D., Bowen, C. M. & Michelet, V. Photodynarnic Fluorescent Metal Ion Sensors with Parts per Billion Sensitivity. *J. Am. Chem. Soc.* 120, 3237–3242 (1998).

Wittmann, C., Riedel, K. & Schmid, R. D. Microbial and Enzyme sensors for environmental monitoring. *Handb. Biosens. Electron. Noses*, 299–332 (1997).

Zhang, B.; Cech, T. R. *Nature* 1997, 390, 96–100.

Zillmann, M.; Limauro, S. E.; Goodchild, J. *RNA* 1997, 3, 734–747.

---

The invention claimed is:

1. A method of detecting the presence of an ion, comprising:
   (a) contacting a nucleic acid enzyme, wherein the enzyme is dependent on the ion to produce a product from a substrate, with a sample suspected of containing the ion; and
   (b) measuring an amount of the product produced;
   wherein the ion is in the presence of other ions, and the ion is $Pb^{2+}$; and
   wherein the substrate comprises a fluorophore and the enzyme comprises a quencher of the fluorophore, or the enzyme comprises a fluorophore and the substrate comprises a quencher of the fluorophore.

2. The method of claim 1, wherein the nucleic acid enzyme comprises a deoxyribozyme.

3. The method of claim 1, wherein the nucleic acid enzyme and the substrate comprise separate nucleic acid strands.

4. The method of claim 3, wherein a 5'-end of the substrate comprises the fluorophore.

5. The method of claim 3, wherein a 3'-end of the enzyme comprises the quencher for the fluorophore.

6. The method of claim 3, wherein the fluorophore is TAMRA.

7. The method of claim 6, wherein the quencher is DABCYL.

8. The method of claim 3, wherein the enzyme is linked to a support.

9. The method of claim 3, wherein the substrate comprises at least one ribonucleotide.

10. The method of claim 3, wherein the substrate comprises the nucleic acid sequence of SEQ ID NO:2.

11. The method of claim 2, wherein the deoxyribozyme comprises a single strand.

12. The method of claim 11, wherein the single strand comprises the fluorophore.

13. The method of claim 11, wherein the single strand further comprises the quencher for the fluorophore.

14. The method of claim 11, wherein the single strand comprises the nucleic acid sequence of SEQ ID NO:1.

15. The method of claim 14, wherein the single strand further comprises the nucleic acid sequence of SEQ ID NO:2.

16. The method of claim 1, wherein the product comprises a nucleic acid.

17. The method of claim 16, wherein the product comprises the fluorophore.

18. The method of claim 16, wherein the product comprises the fluorophore quencher.

19. The method of claim 1, wherein the sample suspected of containing the ion comprises a water sample.

20. The method of claim 1, wherein the sample suspected of containing the ion comprises a bodily fluid.

21. The method of claim 20, wherein the bodily fluid is blood.

22. The method of claim 1, wherein the measuring comprises a measurement of fluorescence.

23. The method of claim 22, wherein the measurement of fluorescence is selected from the group consisting of fluorescence intensity, fluorescence lifetime, and anisotropy.

24. The method of claim 23, wherein an increase in fluorescence is indicative of the presence of the ion.

25. The method of claim 1 wherein the nucleic acid enzyme is cart of an array of nucleic acid enzymes.

26. The method of claim 1, further comprising:
   (c) comparing the measurement obtained in (b) with that of a standard curve created using known concentrations of the ion.

27. The method of claim 26, wherein the nucleic acid enzyme comprises a deoxyribozyme.

28. The method of claim 26, wherein the nucleic acid enzyme and the substrate comprise separate nucleic acid strands.

29. The method of claim 28, wherein a 5'-end of the substrate comprises the fluorophore.

30. The method of claim 29, wherein a 3'-end of the enzyme comprises the quencher for the fluorophore.

31. The method of claim 28, wherein the fluorophore is TAMRA.

32. The method of claim 31, wherein the quencher is DABCYL.

33. The method of claim 28, wherein the enzyme is linked to a support.

34. The method of claim 28, wherein the substrate comprises the nucleic acid sequence of SEQ ID NO:2.

35. The method of claim 27, wherein the deoxyribozyme comprises a single strand.

36. The method of claim 35, wherein the single strand comprises the fluorophore.

37. The method of claim 26, wherein the product comprises a nucleic acid.

38. The method of claim 37, wherein the product comprises the fluorophore.

39. The method of claim 37, wherein the product comprises the fluorophore quencher.

40. The method of claim 26, the sample suspected of containing the ion comprises a water sample.

41. The method of claim 26, wherein the sample suspected of containing the ion comprises a bodily fluid.

42. A method of detecting the presence of an ion, comprising:
(a) contacting a nucleic acid enzyme, wherein the enzyme is dependent on the ion to produce a product from a substrate, with a sample suspected of containing the ion; and
(b) measuring an amount of the product produced; wherein the ion is in the presence of other ions, and the ion is $Pb^{2+}$;
the substrate comprises a fluorophore and the enzyme comprises a quencher of the fluorophore, or the enzyme comprises a fluorophore and the substrate comprises a quencher of the fluorophore;
the nucleic acid enzyme comprises a deoxyribozyme;
the nucleic acid enzyme and the substrate comprise separate nucleic acid strands; and the measuring comprises a measurement of fluorescence.

43. The method of claim 42, wherein the substrate comprises at least one ribonucleotide.

44. The method of claim 42, wherein the sample suspected of containing the ion comprises a water sample.

45. The method of claim 42, wherein the sample suspected of containing the ion comprises a bodily fluid.

46. The method of claim 42, wherein the measurement of fluorescence is by anisotropy.

47. The method of claim 42, further comprising:
(c) comparing the measurement obtained in (b) with that of a standard curve created using known concentrations of the ion.

48. The method of claim 42, further comprising producing the sample by dissolving a solid.

49. The method of claim 48, wherein the solid comprises paint.

50. The method of claim 48, wherein the solid comprises soil.

51. The method of claim 42 wherein the method has a selectivity for $Pb^{2+}$ greater than 80 fold over other divalent metal ions.

52. The method of claim 47, wherein the substrate comprises at least one ribonucleotide.

53. The method of claim 47, wherein the sample suspected of containing the ion comprises a water sample.

54. The method of claim 47, wherein the sample suspected of containing the ion comprises a bodily fluid.

55. The method of claim 47, wherein the measurement of fluorescence is by anisotropy.

56. The method of claim 47, further comprising producing the sample by dissolving a solid.

57. The method of claim 56, wherein the solid comprises paint.

58. The method of claim 56, wherein the solid comprises soil.

59. The method of claim 47 wherein the method has a selectivity for $Pb^{2+}$ greater than 80 fold over other divalent metal ions.

60. The method of claim 48, wherein the substrate comprises at least one ribonucleotide.

61. The method of claim 48, wherein the measurement of fluorescence is by anisotropy.

62. The method of claim 48 wherein the method has a selectivity for $Pb^{2+}$ greater than 80 fold over other divalent metal ions.

63. The method of claim 51, wherein the substrate comprises at least one ribonucleotide.

64. The method of claim 51, wherein the sample suspected of containing the ion comprises a water sample.

65. The method of claim 51, wherein the sample suspected of containing the ion comprises a bodily fluid.

66. The method of claim 51, wherein the measurement of fluorescence is by anisotropy.

67. The method of claim 56 wherein the method has a selectivity for $Pb^{2+}$ greater than 80 fold over other divalent metal ions.

68. The method of claim 67, wherein the substrate comprises at least one ribonucleotide.

69. The method of claim 67, wherein the measurement of fluorescence is by anisotropy.

* * * * *

UNITED STATES PATENT AND TRADEMARK OFFICE
CERTIFICATE OF CORRECTION

PATENT NO.        : 7,192,708 B2
APPLICATION NO. : 10/702676
DATED             : March 20, 2007
INVENTOR(S)       : Yi Lu and Jing Li It is certified that error appears in the above-identified patent and that said Letters Patent is hereby corrected as shown below:

On Title page:
Under Foreign Patent Documents, col. 2, please delete "WO 99/143338" and insert --WO 99/13338--.

Title page
In Other Publications
Page 3, col. 2, line 24, please insert a space after the "+".
Page 7, col. 1, line 60, please delete "ml$^1$" and insert --ml$^{-1}$--.
Page 7, col. 2, line 1, please delete "spectrophotemetry" and insert --spectrophotometry--.
Page 7, col. 2, line 54, please delete "RNA$^{phe}$" and insert --RNA$^{Phe}$--.
Page 8, col. 1, line 23, please delete "an" and insert --An--.

Signed and Sealed this

Thirteenth Day of November, 2007

JON W. DUDAS
*Director of the United States Patent and Trademark Office*